(12) United States Patent
Tepe

(10) Patent No.: US 7,732,436 B2
(45) Date of Patent: Jun. 8, 2010

(54) PREPARATION OF HYMENIALDISINE DERIVATIVES AND USE THEREOF

(75) Inventor: Jetze J. Tepe, East Lansing, MI (US)

(73) Assignee: Board Of Trustees Of Michigan State University, East Lansing, MI (US)

( * ) Notice: Subject to any disclaimer, the term of this patent is extended or adjusted under 35 U.S.C. 154(b) by 0 days.

(21) Appl. No.: 11/501,620

(22) Filed: Aug. 9, 2006

(65) Prior Publication Data

US 2006/0293305 A1 Dec. 28, 2006

Related U.S. Application Data

(62) Division of application No. 10/833,871, filed on Apr. 28, 2004.

(60) Provisional application No. 60/471,671, filed on May 19, 2003.

(51) Int. Cl.
*A61P 29/02* (2006.01)
(52) U.S. Cl. .................................. 514/212.06
(58) Field of Classification Search ............. 514/212.06
See application file for complete search history.

(56) References Cited

U.S. PATENT DOCUMENTS

| | | | |
|---|---|---|---|
| 5,565,448 | A | 10/1996 | Nambi et al. |
| 5,591,740 | A | 1/1997 | Chipman et al. |
| 5,616,577 | A | 4/1997 | Nambi et al. |
| 5,621,099 | A | 4/1997 | Annoura et al. |
| 5,834,609 | A | 11/1998 | Horne et al. |
| 6,103,899 | A | 8/2000 | Horne et al. |
| 6,197,954 | B1 | 3/2001 | Horne et al. |
| 6,211,361 | B1 | 4/2001 | Horne et al. |
| 6,218,549 | B1 | 4/2001 | Horne et al. |
| 6,528,646 | B2 | 3/2003 | Horne et al. |
| 2001/0012891 | A1 | 8/2001 | Horne et al. |
| 2003/0060457 | A1 | 3/2003 | Schaffer et al. |
| 2005/0153955 | A1* | 7/2005 | Wan et al. .............. 514/220 |

FOREIGN PATENT DOCUMENTS

| | | |
|---|---|---|
| EP | 1106180 A1 | 6/2001 |
| WO | 0141768 A2 | 6/2001 |
| WO | 03/027275 | 4/2003 |

OTHER PUBLICATIONS

Inoue et al., Inflamm. Res. 50: 65-72 (2001).
Roshak et al., J. Pharmacol. Exp. Ther. 283: 955-961 (1997).
Cimino, et al., Tet. Lett. 23: 767-768 (1982).
Breton and Chabot-Fletcher,J. Pharmacol. Exp. Ther. 282: 459-466 (1997).
Badger et al., J. Pharmacol. Exp. Ther. 290: 587-593 (1999).
Badger et al., Osteoarthritis Cartilage 8: 434-443 (2000).
Meijer et al., Chem. Biol. 7: 51-63 (2000).
Tasdemir et al., J. Med. Chem. 45: 529-532 (2002).
Annoura and Tatsuoka, Tet. Let. 36: 413-416 (1995).
Mizuno et al., Chem. Pharm. Bull. 47: 246-256 (1999).
Cho et al., J. Heterocycl. Chem. 34: 87-91 (1997).
Xu et al., J. Org. Chem. 62:456-464 (1997).
Prager and Tsopelas, Aust. J. Chem. 43: 367-374 (1990).
Prager and Tsopelas, Aust. J. Chem. 45: 1771-1777(1992).
Aikawa et al., Inflamm. Res. 51: 188-194 (2002).
Dignam et al., Nucl. Acids Res. 11: 1475-1489 (1983).

* cited by examiner

*Primary Examiner*—Bruck Kifle
(74) *Attorney, Agent, or Firm*—Medlen & Carroll, LLP

(57) ABSTRACT

The synthesis and biological activity of indoloazepines and acid amine salts thereof which are structurally related to naturally-occurring hymenialdisine is disclosed. Naturally-occurring hymenialdisine obtained from the sponge is a potent inhibitor of production of cytokines interleukin-2 (IL-2) and tumor necrosis factor-α (TNF-α). The chemically-synthesized indoloazepines of the invention also inhibit production of IL-2 and TNF-α. The indoloazepines are useful for treating inflammatory diseases, particularly diseases associated with kinases NF-κB or GSK-3β activation or NF-κB activated gene expression products. The indoloazepines are useful for the treatment of cancer by the inhibition of kinases CHK1 and CHK2.

6 Claims, 7 Drawing Sheets

PREPARATION OF HYMENIALDISINE DERIVATIVES AND USE THEREOF

CROSS-REFERENCE TO RELATED APPLICATION

This application is a divisional of copending application Ser. No. 10/833,871 filed on Apr. 28, 2004. This application claims priority to Provisional Application Ser. No. 60/471,671, filed May 19, 2003.

STATEMENT REGARDING FEDERALLY SPONSORED RESEARCH OR DEVELOPMENT

Not applicable.

REFERENCE TO A "COMPUTER LISTING APPENDIX SUBMITTED ON DISC"

Enclosed is Computer Listing Appendix submitted on disc.

BACKGROUND OF THE INVENTION (1) Field of the Invention

The present invention related to the synthesis and biological activity of indoloazepines and acid amine salts thereof which are structurally related to naturally-occurring hymenialdisine. The chemically-synthesized indoloazepines inhibit production of IL-2 and TNF-α. Exposure of the chemically-synthesized indoloazepine to mammalian Jurkat leukemia T-cells and THP-1 cells results in a dose response inhibition of IL-2 production and TNF-α production, respectively. The indoloazepines are useful for treating inflammatory diseases, particularly diseases associated with NF-κB or GSK-3β activation and NF-κB activated gene expression.

(2) Description of Related Art

Elevated levels of cytokines, such as interleukin-1 (IL-1), interleukin-2 (IL-2), interleukin-6 (IL-6), interleukin-8 (IL-8), and tumor necrosis factor-α (TNF-α) have been linked to many inflammatory disorders including Crohn's disease and psoriasis, and play an essential role in the pathogenesis of rheumatoid arthritis and osteoarthritis (Gerard et al., Nat. Immunol. 2: 108-115 (2001); Inoue et al., Inflamm. Res. 50: 65-72 (2001); Polisson, Curr. Rheumatol. Rep. 3: 489-495 (2001); Miossec, Cell Mol. Biol. (Noisy-le-grand) 47: 675-678 (2001); Roshak et al., J. Pharmacol. Exp. Ther. 283: 955-961 (1997); Harris, N. Engl. J. Med. 322: 1277-1289 (1990)).

Using anti-inflammatory drugs to inhibit cytokines, in particular TNF-α, has been successful in several clinical trials for treating rheumatoid arthritis (Moreland, J. Rheumatol. 26 Suppl. 57: 7-15 1999); Moreland, et al., N. Engl. J. Med. 337: 141-147 (1997)). However, there is variability in responses to these anti-inflammatory drugs because of the complex network of alternative cytokine mediated pathways (Miossec, Cell Mol. Biol. (Noisy-le-grand) 47: 675-678 (2001); Handel et al., Clin. Exp. Pharmacol. Physiol. 27: 139-144 (2000)). Using drugs which inhibit transcription factors that control the expression of several pro-inflammatory mediators, such as the nuclear transcription factor NF-κB, may overcome response variability and may provide an alternative strategy for treating a wide variety of inflammatory disorders (Makarov, Arthritis Res. 3: 200-206 (2001); Tak, J. Clin. Invest. 107: 7-11 (2001); Roshak et al., Curr. Opin. Pharmacol. 2: 316-321 (2002); Yamamoto and Gaynor, J. Clin. Invest. 107: 135-142 (2001); Feldmann et al., Ann. Rheum. Dis. 61 Suppl. 2: ii13-18 (2002); Barnes and Karin, N. Engl. J. Med. 336: 1066-1071 (1997); Lee and Burckart, J. Clin. Pharmacol. 38: 981-993 (1998); Baldwin, Ann. Rev. Immunol. 14: 649-683 (1996); Miagkov et al., Proc. Natl. Acad. Sci. USA 95: 13859-13864 (1998); Guttridge et al., Mol. Cell Biol. 19: 5785-5799 (1999); Baeuerle and Henkel, Ann. Rev. Immunol. 12: 141-179 (1994)).

Because of its critical role in the regulation of inflammatory responses, NF-κB has become an increasingly significant therapeutic target for controlling diseases such as asthma, rheumatoid arthritis, multiple sclerosis, and Alzheimer's disease (Tak, J. Clin. Invest. 107: 7-11 (2001); Yamamoto and Gaynor, J. Clin. Invest. 107: 135-142 (2001); Barnes and Karin, N. Engl. J. Med. 336: 1066-1071 (1997); Boland, Biochem. Soc. Trans. 29: 674-678 (2001); Hart et al., Am. J. Respir. Crit. Care Med. 158: 1585-1592 (1998); Yamamoto and Gaynor, Curr. Mol. Med. 1: 287-296 (2001)).

Hymenialdisine is a bromopyrrole alkaloid which was originally isolated from the marine sponges *Axinella verrucosa* and *Acantella aurantiaca*. Its structure was established on the basis of X-ray crystallography (Cimino et al., Tet. Lett. 23: 767-768 (1982)). The structure of hymenialdisine is shown in FIG. 1A. Hymenialdisine has been found to inhibit various proinflammatory cytokines, such as IL-1, IL-6, IL-8, and nitric oxide in a variety of cell lines (Inoue et al., Inflamm. Res. 50: 65-72 (2001); Roshak et al., J. Pharmacol. Exp. Ther. 283: 955-961 (1997); Breton and Chabot-Fletcher, J. Pharmacol. Exp. Ther. 282: 459-466 (1997); Badger et al., J. Pharmacol. Exp. Ther. 290: 587-593 (1999)). Investigation of the promising anti-inflammatory properties of hymenialdisine revealed that it inhibits cytokine production by inhibiting the NF-κB signaling pathway (Roshak et al., J. Pharmacol. Exp. Ther. 283: 955-961 (1997); Breton and Chabot-Fletcher, J. Pharmacol. Exp. Ther. 282: 459-466 (1997); Badger et al., J. Pharmacol. Exp. Ther. 290: 587-593 (1999); Badger et al., Osteoarthritis Cartilage 8: 434-443 (2000)). Gel shift analysis showed that this inhibition was that hymenialdisine selectively reduced NF-κB nuclear binding and not the binding of other transcription factors such as C/EBP, AP-1, or SP1 (Roshak et al., J. Pharmacol. Exp. Ther. 283: 955-961 (1997)).

Recently, Meijer et al. reported that the potent NF-κB inhibitor hymenialdisine acts as a competitive nanomolar inhibitor of the cyclin-dependent kinases GSK-3β and CK1 (Meijer et al., Chem. Biol. 7: 51-63 (2000)). Crystallographic data showed that hymenialdisine binds to the ATP binding pocket of the GSK-3β and CK1 kinases (Meijer et al., Chem. Biol. 7: 51-63 (2000)). Considering the potential relationship between NF-κB activation and GSK-3, that might suggest a potential pathway for this kinase inhibitor (Meijer et al., Chem. Biol. 7: 51-63 (2000); Ali et al., Chem. Rev. 101: 2527-2540 (2001); Schwabe and Brenner, Am. J. Physiol. Gastrointest. Liver Physiol. 283: G204-211 (2002)). In addition, Ireland et al. identified hymenialdisine as a very potent MEK-1 inhibitor with low nanomolar $IC_{50}$ values. This suggests that hymenialdisine may be useful as an antiproliferative agent (Tasdemir et al., J. Med. Chem. 45: 529-532 (2002)).

Hymenialdisine and various derivatives thereof such as debromohymenialdisine have been disclosed in the following patents and published patent applications.

U.S. Pat. No. 5,565,448 to Nambi et al. discloses medicants which contain hymenialdisine or debromohymenialdisine and which are used to inhibit protein kinase C and U.S. Pat. No. 5,616,577 to Nambi et al. discloses methods using hymenialdisine or debromohymenialdisine to inhibit protein kinase C.

U.S. Pat. No. 5,591,740 to Chipman et al. discloses using compositions comprising hymenialdisine or debromohymenialdisine to treat osteoarthritis.

U.S. Pat. No. 5,621,099 to Annoura et al. discloses a method for synthesizing hymenialdisine, bromohymenialdisine, and related compounds.

U.S. Pat. Nos. 5,834,609, 6,103,899, and 6,218,549, all to Horne et al. disclose bicyclic aminoimidizole compounds which have anti-tumor and antimicrobial activity.

U.S. Pat. Nos. 6,197,954 B1, 6,211,361, 6,528,646, and published U.S. Patent Application No. 2001/0012891A1, all to Horne et al., disclose processes for synthesizing hymenialdisine, related compounds, and their intermediates.

Published U.S. Patent Application No. 20030060457A1 to Schaffer et al. discloses that hymenialdisine is a cdk inhibitor which can be used as an inhibitor of gene expression, replication, and reactivation in pathogenic agents.

EP1106180A1 and WO0141768A2 to Meijer disclose using hymenialdisine and related compounds such as debromohymenialdisine to inhibit cyclin dependent kinases, GSK-3β, and casein kinase 1 for preventing and treating neurodegenerative disorders such as Alzheimer's disease, diabetes, inflammatory pathologies, and cancers.

DNA replication is a process that requires great accuracy and relies on surveillance mechanisms, which monitor DNA damage and initiate DNA repair (Zhou, B.-B. S., et al., Nature 408 433-439 (2000)). The inability to carry out DNA repair often leads to the transformation of normal cells into malignancies (Martin, N. M. B., J. Photochem. Photobiol. B 63 162-170 (2001)). Upon DNA damage, cell cycle checkpoints get activated, which delay cell cycle progression and allow DNA repair. A multi-faceted involvement of these checkpoint pathways regulates DNA repair, (Zhou, B.-B. S., et al., Nature 408 433-439 (2000; Martin, N. M. B., J. Photochem. Photobiol. B 63 162-170 (2001); and Zhao, S., et al., Nature 405, 473 (2000)) telomere length (Naito, T., et al., Nat. Genet. 20 203-206 (1998); Ritchie, K. B., et al., Mol. Cell Biol. 10 6065-6075 (1999)) and the induction of apoptotic cell death (Zhou, B.-B. S., et al., Nature 408 433-439 (2000); and Lowe, S. W., et al., Nature 362 847-849 (1993)). Protein kinases regulate a host of cellular processes such as growth and differentiation, cell proliferation and apoptosis (Sielecki, T. M., et al., J. Med. Chem. 43 1-18 (2000); Sridhar, R., et al., Pharm. Res. 17 1345-1353 (2000); Traxler, P., et al., J. Med. Res. Rev. 21 499-512 (2001); Scapin, G., Drug Discovery Today 7. (2001); Toogood, P. L., Med. Res. Rev. 21 487-498 ((2001); and Bridges, A. J., Chem. Rev. 101 2541-2572 (2001)). DNA damage caused by radiation or chemotherapy triggers the DNA damage-responsive protein kinases ATM and ATR, which activate Chk1 and Chk2. Chk1 and Chk2 in turn phosphorylate Cdc25 and prevent Cdc2 activation, resulting in cell cycle arrest (Curman, D., et al., J. Biol. Chem. 276 17914-17919 (2001)). Hence, small molecules that can inhibit the checkpoints may enhance the efficacy of DNA damaging chemotherapeutics or radiation therapy (Rundle, N. T., et al., J. Biol. Chem. 276 48231-48236 (2001); Jackson, J. R., et al., Cancer Res. 60 566-572 (2000); Koniaras, K., et al., Oncogene 20 7453-7463 (2001); Zhou, B.-B. S., et al., Cancer Biol. Ther. 2 S16-S22 (2003); Yu, Q., et al., Cancer Res. 62 5743-5748 (2002)).

In light of the prior art, there remains a need for other small molecules that have activities which exhibit a similar or better pharmacological profile to hymenialdisine and which are simple and inexpensive to prepare.

SUMMARY OF THE INVENTION

The synthesis and biological activity of indoloazepines and acid amine salts thereof which are structurally related to naturally-occurring hymenialdisine is disclosed. Naturally-occurring hymenialdisine obtained from the sponge is a potent inhibitor of production of interleukin-2 (IL-2) ($IC_{50}$=2.4 µM) and tumor necrosis factor-α (TNF-α) ($IC_{50}$=1.4 µM). The chemically-synthesized indoloazepine also inhibits production of IL-2 and TNF-α. Exposure of the chemically-synthesized indoloazepine to mammalian Jurkat leukemia T-cells and THP-1 cells resulted in a dose response inhibition of IL-2 production ($IC_{50}$=3.5 µM) and TNF-α production ($IC_{50}$=8.2 µM), respectively. The indoloazepines are useful for treating inflammatory diseases, particularly diseases associated with NF-κB activation.

The chemically-synthesized indoloazepine also inhibits the kinase CHK2 ($IC_{50}$=8 nM. The indolozaepines are useful for treating cancer.

Therefore, the present invention provides a compound of the formula

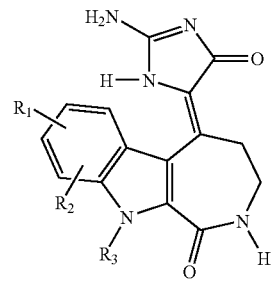

and acid amine salts thereof, wherein $R_1$, $R_2$, and $R_3$ are moieties such that the compound inhibits kinases or NF-κKB or NF-κB mediated gene products. In a further embodiment, $R_1$, $R_2$, and $R_3$ are moieties such that the compound inhibits a cyclin kinase, particularly wherein the cyclin kinase is GSK-3β or CDK-1. In a further embodiment, $R_1$, $R_2$, and $R_3$ are moieties such that the compound are inhibitors of checkpoint kinases, particularly wherein the kinase is CHK2. In a further embodiment, $R_1$, $R_2$, and $R_3$ are each selected from the group consisting of hydrogen, methyl, alkyl containing 1 to 6 carbon atoms, halo, aryl, acyl, hydroxyl, amine, thiol, ester, ether, and amide. In a preferred embodiment, $R_1$, $R_2$, and $R_3$ are each hydrogen.

The present invention further provides a compound of the formula

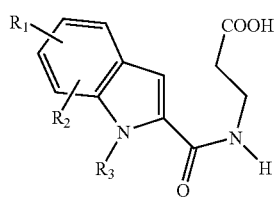

and acid amine salts thereof, wherein $R_1$, $R_2$, and $R_3$ are non-reactive groups. In a preferred embodiment, $R_1$, $R_2$, and $R_3$ are each selected from the group consisting of hydrogen, methyl, alkyl containing 1 to 6 carbon atoms, halo, aryl, acyl, hydroxyl, amine, thiol, ester, ether, and amide. In a particularly preferred embodiment, $R_1$, $R_2$, and $R_3$ are each hydrogen.

The present invention further provides a compound of the formula

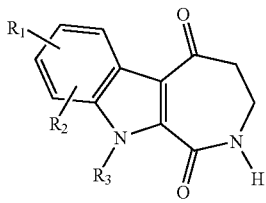

and acid amine salts thereof, wherein $R_1$, $R_2$, and $R_3$ are non-reactive groups. In a preferred embodiment, $R_1$, $R_2$, and $R_3$ are each selected from the group consisting of hydrogen, methyl, alkyl containing 1 to 6 carbon atoms, halo, aryl, acyl, hydroxyl, amine, thiol, ester, ether, and amide. In a particularly preferred embodiment, $R_1$, $R_2$, and $R_3$ are each hydrogen.

The present invention further provides a compound of the formula

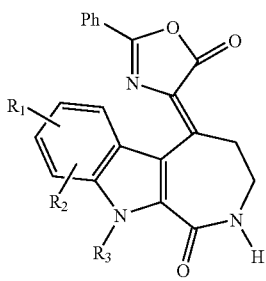

and acid amine salts thereof, wherein $R_1$, $R_2$, and $R_3$ are non-reactive groups. In a preferred embodiment, $R_1$, $R_2$, and $R_3$ are each selected from the group consisting of hydrogen, methyl, alkyl containing 1 to 6 carbon atoms, halo, aryl, acyl, hydroxyl, amine, thiol, ester, ether, and amide. In a particularly preferred embodiment, $R_1$, $R_2$, and $R_3$ are each hydrogen.

The present invention further provides a process for the preparation of a compound (IV) of the formula

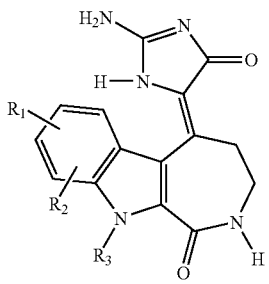

herein $R_1$, $R_2$, and $R_3$ are which are non-reactive, which comprises (a) reacting a first compound (I) of the formula

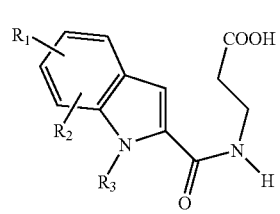

with methyl sulfonic acid and phosphorus pentoxide at elevated temperatures to form a second compound (II) of the formula

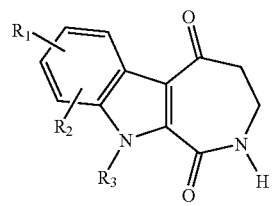

(b) reacting compound (II) with phenyl oxazolone and a transition metal catalyst in a solvent to form compound (III) of the formula and (c) reacting compound (III) with thiourea and a base in a solvent to form the compound (IV). In a further embodiment of the process, in step (b) the transition metal catalyst is titanium chloride and the solvent is tetrahydrofuran. In a further embodiment of the process, in step (c) the base is lithium hydride and the solvent is ethanol. In a further still embodiment of the process, the compound (I) is formed by reacting a compound (V)

with an aqueous base solution, preferably wherein the base is lithium hydroxide.

The present invention further provides a method for inhibiting a disease in an animal, preferably a human, associated with a kinase or NF-κB activation which comprises administering a compound of the formula

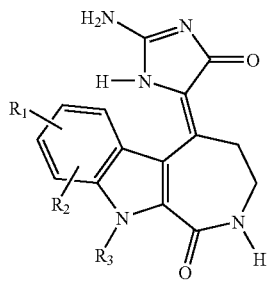

and acid amine salts thereof, wherein $R_1$, $R_2$, and $R_3$ are moieties such that the compound inhibits the kinase, NF-κB activation or NF-κB mediated gene products, the compound being administered to the animal in an amount sufficient to substantially inhibit the disease. In a further embodiment, $R_1$, $R_2$, and $R_3$ are moieties such that the compound inhibits a cyclin kinase, particularly wherein the cyclin kinase is GSK-3β or CDK-1. In a further embodiment, $R_1$, $R_2$, and $R_3$ are moieties such that the compounds are inhibitors of checkpoint kinases, particularly wherein the kinase is CHK2. In a further embodiment, $R_1$, $R_2$, and $R_3$ are each selected from the group consisting of hydrogen, methyl, alkyl containing 1 to 6 carbon atoms, halo, aryl, acyl, hydroxyl, amine, thiol, ester, ether, and amide. In a preferred embodiment, $R_1$, $R_2$, and $R_3$ are each hydrogen.

In a preferred embodiment of the method, the disease associated with NF-κB activation is an inflammatory disorder. In a more preferred embodiment, the disease associated with NF-κB activation is selected from the group consisting of rheumatoid arthritis, inflammatory bowel disease, asthma, dermatosis, autoimmune disease, tissue and organ rejection, Alzheimer's disease, stroke, atherosclerosis, restenosis, cancer, viral infections, osteoarthritis, osteoporosis, and Ataxia Telangiectasia.

In a preferred embodiment of the method, the disease associated with inhibition checkpoint kinases is cancer.

The present invention further provides a method for inhibiting production of cytokines in an animal, preferably a human, which comprises administering a compound of the formula

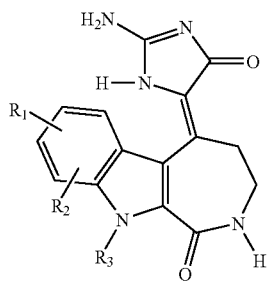

and acid amine salts thereof, wherein $R_1$, $R_2$, and $R_3$ are moieties such that the compound inhibits the cytokines, the compound being administered to the animal in an amount sufficient to inhibit production of the cytokines. In a further embodiment, $R_1$, $R_2$, and $R_3$ are moieties such that the compound inhibits a cyclin kinase, particularly wherein the cyclin kinase is GSK-3β or CDK-1. In a further embodiment, $R_1$, $R_2$, and $R_3$ are moieties such that the compound are inhibitors of checkpoint kinases, particularly wherein the kinase is CHK2. In a further embodiment, $R_1$, $R_2$, and $R_3$ are each selected from the group consisting of hydrogen, methyl, alkyl containing 1 to 6 carbon atoms, halo, aryl, acyl, hydroxyl, amine, thiol, ester, ether, and amide. In a preferred embodiment, $R_1$, $R_2$, and $R_3$ are each hydrogen.

In a preferred embodiment of the method, the cytokines are produced by activation of the NF-κB pathway. In a more preferred embodiment, the cytokines are selected from the group consisting of IL-2, IL-6, IL-8, TNF-α, and combinations thereof.

OBJECTS

It is an object of the present invention to provide small molecules and processes for synthesizing which are useful for treating inflammatory diseases.

It is a further object of the present invention to provide small molecules and processes for synthesizing which are useful for treating diseases associated with NF-κB activation.

It is further an object of the present invention to provide small molecules and processes for synthesizing which are useful for treating diseases such as cancer.

These and other objects of the present invention will become increasingly apparent with reference to the following drawings and preferred embodiments.

DETAILED DESCRIPTION OF THE INVENTION

Figure 1A:
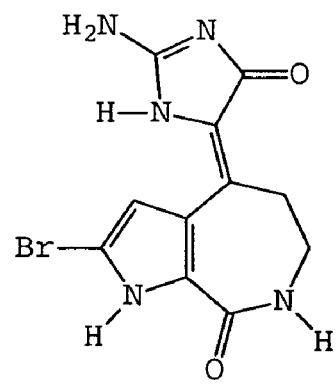
FIG. 1A shows the structure of naturally-occurring hymenialdisine 1

All patents, patent applications, government publications, government regulations, and literature references cited in this specification are hereby incorporated herein by reference in their entirety. In case of conflict, the present description, including definitions, will control.

The present invention includes all hydrates, solvates, complexes, and prodrugs of the compounds of this invention. Prodrugs are any covalently bonded compounds which in vivo releases the active parent drug having the formula The present invention further includes compounds and prodrugs of such compounds which have the formula

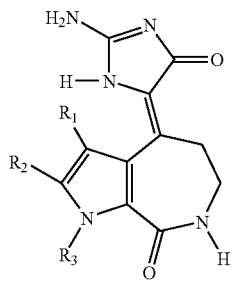

and acid amine salts thereof, wherein $R_1$, $R_2$, and $R_3$ are moieties such that the compound inhibits NF-κB in human Jurkat Leukemia T-cells activated to transcribe NF-κB mediated gene transcription by phorbol myristate acetate (PMA). In a further embodiment, $R_1$, $R_2$, and $R_3$ are moieties such that the compound inhibits a cyclin kinase, particularly wherein the cyclin kinase is GSK-3β or CDK-1. In a further embodiment, $R_1$, $R_2$, and $R_3$ are each independently selected from the group consisting of methyl, alkyl, heteroalkyl, substituted alkyl, aryl, heteroaryl, substituted aryl, cyclic, heterocyclic, substituted cyclic, and combinations thereof; and, the $R_1$ and $R_2$ can be interconnected. Preferably, the $R_1$ and $R_2$ are interconnected members of an aryl or cyclic ring which can be substituted or comprise heteroatoms or both. Preferably, $R_3$ is hydrogen. The term "halo" includes F, Cl, Br, and I. The alkyl, aryl, acyl, cyclo includes substituted and heteroatom species as well as the unsubstituted species. If a chiral center or another form of an isomeric center is present in a compound of the present invention, all forms of such isomer or isomers, including enantiomers and diastereomers, are intended to be covered herein. Compounds containing a chiral center may be used as a racemic mixture, an enantiomerically enriched mixture, or the racemic mixture may be separated using well-known techniques and an individual enantiomer may be used alone. In cases in which compounds have unsaturated carbon-carbon double bonds, both the cis (Z) and trans (E) isomers are within the scope of this invention. In cases wherein compounds may exist in tautomeric forms, such as keto-enol tautomers, each tautomeric form is contemplated as being included within this invention whether existing in equilibrium or predominantly in one form.

The compounds disclosed herein are provided in organic solvents such as DMSO or other organic solvents which are pharmaceutically acceptable. The compounds disclosed herein are also provided as their amine acid salts. For example, the compounds herein are prepared in an appropriate solvent as taught herein. An excess of an acid such as acetic, hydrochloric, hydrobromic, hydrofluoric, maleic, methansulfonic, phosphoric, succinic, sulfuric, trifluoroacetic, or sulfuric acid is added which produces the compound as its acid salt. The acid salts of the compounds are more soluble in water and other pharmaceutically acceptable aqueous solutions.

In light of the need for small molecule inhibitors of NF-κB mediated gene transcription, the present invention provides chemical synthesis and methods of use for the compounds of the above formula. In a preferred embodiment, the compounds have the formula

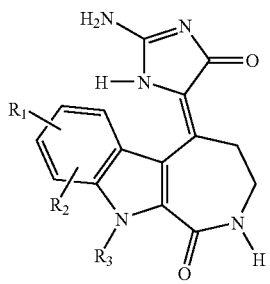

and acid amine salts thereof, wherein $R_1$, $R_2$, and $R_3$ are moieties such that the compound inhibits NF-κB in human Jurkat Leukemia T-cells activated to transcribe NF-κB mediated gene transcription by phorbol myristate acetate (PMA). In a further embodiment, $R_1$, $R_2$, and $R_3$ are moieties such that the compound inhibits a cyclin kinase, particularly wherein the cyclin kinase is GSK-3β or CDK-1. In a further embodiment, $R_1$, $R_2$, and $R_3$ are each independently selected from the group consisting of hydrogen, methyl, alkyl containing 1 to 6 carbon atoms, halo, aryl, acyl, hydroxyl, amine, thiol, ester, ether, and amide. In a preferred embodiment, $R_1$, $R_2$, and $R_3$ are each hydrogen.

In light of the need for small molecule inhibitors of checkpoint kinases, the present invention provides chemical synthesis and methods of use for the compounds of the above formula. In a preferred embodiment, the compounds have the formula

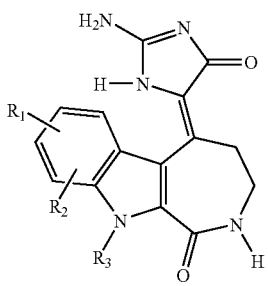

and acid amine salts thereof, wherein $R_1$, $R_2$, and $R_3$ are moieties such that the compound inhibits checkpoint kinases such as Chk1 and CHK2. In a further embodiment, $R_1$, $R_2$, and $R_3$ are each independently selected from the group consisting of hydrogen, methyl, alkyl containing 1 to 6 carbon atoms, halo, aryl, acyl, hydroxyl, amine, thiol, ester, ether, and amide. In a preferred embodiment, $R_1$, $R_2$, and $R_3$ are each hydrogen.

In a preferred embodiment, the present invention provides the indoloazepine, compound 2, which has the formula

Figure 1B:
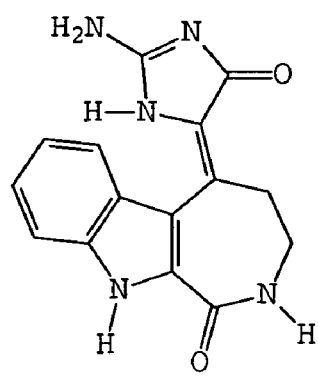
FIG. 1B shows the structure for chemically-synthesized indoloazepine compound 2.
Figure 1C:
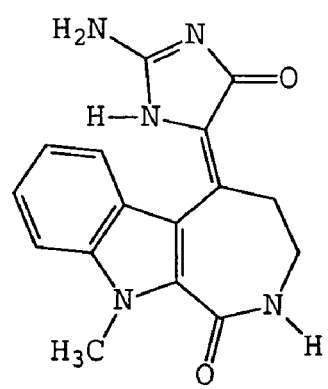
FIG. 1C shows the structure for chemically-synthesized indoloazepine compound 3.

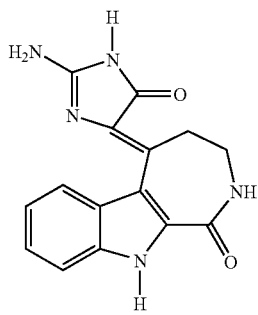

and acid amine salts thereof. A comparison of compound 2 to hymenialdisine 1 and compound 3, a methylated variant of compound 2, is shown in FIGS. 1A, 1B, and 1C.

Hymenialdisine 1 inhibits a wide variety of proinflammatory cytokines such as IL-2, IL-6, IL-8, and nitric oxides through inhibition of the NF-κB signaling pathway. Compound 2 also substantially inhibits NF-κB mediated cytokine production. The examples herein show that compound 2, in particular, inhibits IL-2 and TNF-α production with $IC_{50}$ values similar to the $IC_{50}$ values for the naturally-occurring hymenialdisine 1. Compound 2 and its derivatives, including compounds with the above formula, substantially inhibits NF-κB mediated cytokine production, including IL-2, IL-6, IL-8, and nitric oxides. At the concentrations tested, compound 3 did not appear to have significant inhibitory activity. Because compounds 2 and 3, and derivatives thereof, including compounds with the above formula, can be chemically synthesized, they provide a convenient source of hymenialdisine-related small molecules which can be used for treating a variety of inflammatory diseases where it is desirable to inhibit NF-κB-mediated cytokine production. The compounds, like hymenialdisine, are also GSK-3β inhibitors (See WO 03/027275 to Hellberg et al.).

The naturally-occurring hymenialdisine 1 and debromohymenialdisine inhibit the checkpoint kinases CHK1 and CHK2 at low micromolar concentrations. Compound 2 is a much more potent and selective inhibitor of inhibited checkpoint kinases than the naturally-occurring hymenialdisine 1 and debromohymenialdisine. The examples herein show that compound 2, in particular, inhibits Chk1 with an $IC_{50}$ value of 237 nanoMolar concentration and inhibits CHK2 with an $IC_{50}$ value of 8 nanoMolar concentration. This shows that the synthetically prepared indoloazepines have an improved overall kinase profile and significantly improves its kinase selectivity.

Therefore, the present invention provides pharmaceutical compositions comprising one or more of the compounds with the above formula which are inhibitors of transcription factor NF-κB, and methods for treating diseases in which activation of NF-κB or activity of GSK-3β is implicated. More specifically, the present invention provides compositions and methods of treatment of a variety of diseases associated with NF-κB or GSK-3β activation or GSK-3β inflammatory disorders; particularly rheumatoid arthritis, inflammatory bowel disease, and asthma; dermatosis, including psoriasis and atopic dermatitis; autoimmune diseases; tissue and organ rejection; Alzheimer's disease; stroke; atherosclerosis; restenosis; cancer, including Hodgkin's disease; a variety of viral infections, including AIDS; osteoarthritis; osteoporosis; glaucoma; and, Ataxia Telangiectasia by administering to an animal or human in need thereof a compound comprising the above formula.

Therefore, the present invention also provides pharmaceutical compositions comprising one or more of the compounds with the above formula which are inhibitors of checkpoint kinases, and methods for treating diseases in which checkpoint kinases are implicated. More specifically, the present invention provides compositions and methods of treatment of a variety of diseases associated with checkpoint kinases such as cancer.

Figure 4:
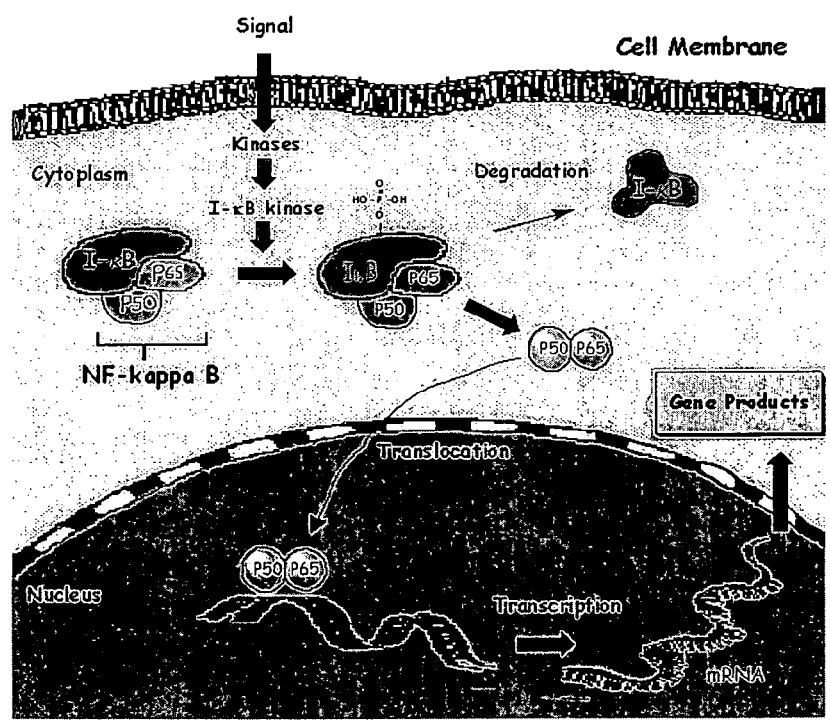
FIG. 4 is a cartoon illustrating the role of NF-κB in activating transcription of particular genes such as those encoding various cytokines.

Without intending to be bound by any particular theory, the inhibition of NF-κB by the compounds of the above formula is believed to be exerted in the nucleus of the cell as shown in FIG. 4. Under normal cellular conditions, NF-κB is sequestered in a complex with IκB. In response to a signal by an unknown pathway, a kinase phosphorylates IκB in the cytoplasm. IκB then degrades which releases the NF-κB. The NF-κB enters the nucleus and is believed to undergo additional phosphorylation by GSK-3β. The phosphorylated NF-κB can then bind to the cellular DNA which stimulates transcription of genes encoding cytokines such as IL-1, IL-2, IL-6, IL-8, and TNF-α. It also has a role in stimulating transcription of genes which are involved in cell growth such as DNA repair, cell division, and cell survival. The compounds of the above formula likely inhibit the phosphorylation of NF-κB by GSK-3 by binding to the ATP binding pocket of the GSK-3β. As a result, cytokine production is inhibited and cell growth is inhibited. The above scheme is to be contrasted with the activity of other compounds such as imidizolines which inhibit NF-κB in the cytoplasm, not in the nucleus.

The synthesis of the indol-aldisine or indoloazepine skeleton (compounds 2 and 3 shown in FIG. 1) is shown in Scheme 1 and described in Example 1. It was achieved via a modified route as reported in the synthesis of aldisine (Annoura and Tatsuoka, Tet. Lett. 36: 413-416 (1995); Mizuno et al., Chem. Pharm. Bull. 47: 246-256 (1999); Cho et al., J. Heterocycl. Chem. 34: 87-91 (1997); Xu et al., J. Org. Chem. 62: 456-464 (1997)).

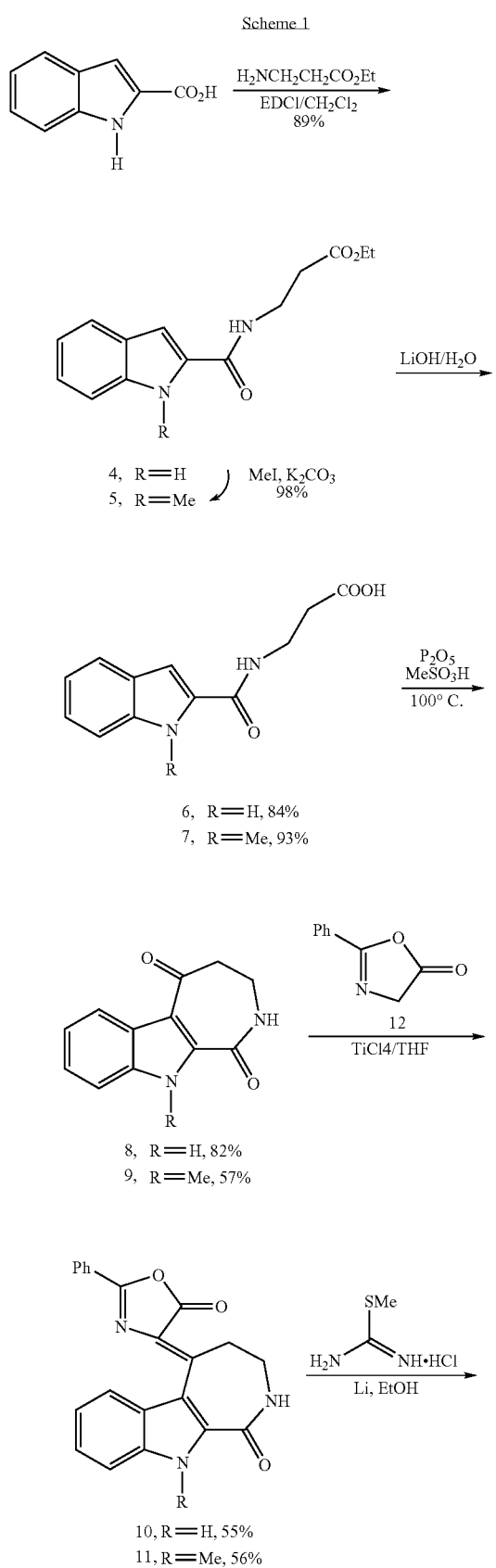

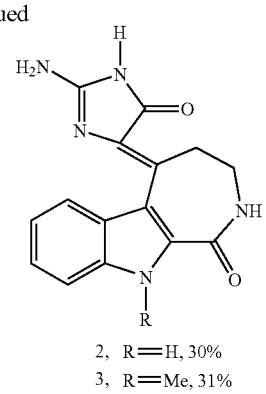

2, R=H, 30%
3, R=Me, 31%

Starting with the commercially available 2-indolecarboxylic acid, condensation with the ethyl ester of β-alanine in the presence of EDCI and DMAP, provided the indole 4. Methylation of the indole nitrogen with MeI and $K_2CO_3$ proceeded in near quantitative yields, rendering the N-methyl indole, which was used for the synthesis of 3. Hydrolysis of esters 4 and 5 followed by the $P_2O_5$/$MeSO_3H$ mediated cyclization provided the key intermediate aldisine derivatives 8 and 9.

The direct condensation of the aldisine derivatives 8 or 9 with the imidazolone precursor (Scheme 2) proved to be unsuccessful similar to earlier reports with the pyrrolazepines (Scheme 2) (Prager and Tsopelas, Aust. J. Chem. 43: 367-374 (1990); Prager and Tsopelas, Aust. J. Chem. 45: 1771-1777 (1992)). However, $TiCl_4$ mediated Aldol condensation with the phenyl oxazolone 12 provided the oxazolone successfully in 55% and 56% yield for compounds 10 and 11, respectively. Treatment of the oxazolone derivatives 10 and 11 with the thiourea under basic conditions provided the final products, indoloazepines (compounds) 2 and 3 in modest yields.

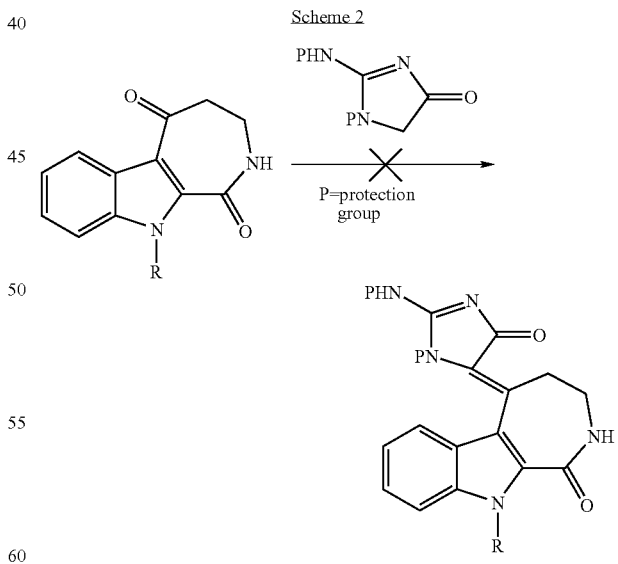

Scheme 2

Hymenialdisine 1 and compounds 2 and 3 were evaluated for their anti-inflammatory activity by examining the transcriptional activity of NF-κB in human Jurkat leukemia T-cells and THP-1 cells (human monocytic leukemia cell line) (Examples 2-5). Exposure of human Jurkat leukemia T-cells to phorbol myristate acetate (PMA/PHA) and THP-1 cells to lipopolysaccharide (LPS), activates NF-κB mediated gene transcription of several pro-inflammatory cytokines, including IL-2, IL-6, IL-8 and TNF-α(Baldwin, Ann. Rev. Immunol. 14: 649-683 (1996); Grilli et al., Int. Rev. Cytol. 143: 1-62 (1993)). The anti-oxidant and non-selective NF-κB inhibitor, pyrrolidinedithiocarbamate (PDTC), has been reported to repress activation of NF-κB and was used as a control in all experiments in addition to an authentic sample of the natural product, hymenialdisine (Grilli et al., Int. Rev. Cytol. 143: 1-62 (1993); Epinat and Gilmore, Oncogene 18: 6896-6909 (1999); Cuzzocrea et al., Br. J. Pharmacol. 135: 496-510 (2002)). The effect of hymenialdisine and compounds 2 and 3 on NF-κB's transcriptional activity was evaluated by measuring the level of IL-2 and TNF-α production using a competitive enzyme immunoassay (EIA). The inhibition of IL-2 was evaluated in Jurkat cells after PMA/PHA activation (Mahon and O'Neill, J. Biol. Chem. 270: 28557-28564 (1995); Lindgren et al., Molec. Immunol. 38V 267-277 (2001)). The inhibition of TNF-α was evaluated in THP-1 cells after LPS activation (Aikawa et al., Inflamm. Res. 51: 188-194 (2002)). NF-κB mediated transcription of IL-2 production was examined by exposing the cells to PDTC or compounds 1-3, 30 minutes prior to PMA activation. After 24 hours, the cell free supernatant fractions were collected and subjected to EIA for the quantification of total IL-2 production.

Compound 2 and the natural product hymenialdisine exhibited potent inhibition of IL-2 and TNF-α production, whereas the N-methyl compound 3 had substantially less IL-2 or TNF-α inhibitory activity. Hymenialdisine and compound 2 were found to inhibit DNA binding by NF-κB. Gel electrophoresis assays indicated that none of the compounds had any notable effect on the DNA binding of the transcription factor AP-1.

Hymenialdisine and compounds 2 and 3 were tested for inhibition of the cyclin dependent kinases CDK1 and GSK-3β using the method of Meijer et al., Chem. Biol. 7: 51-63 (2000). Like hymenialdisine, compound 2 inhibited CDK1 ($IC_{50}=0.4$ μM) and GSK-3β ($IC_{50}=150$ nM). The inhibitory activity of compound 3 was less pronounced.

Thus, compounds which have the formula

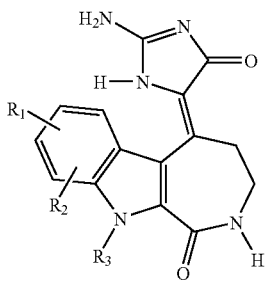

wherein $R_1$, $R_2$, and $R_3$ are moieties such that the compound inhibits NF-κB in human Jurkat Leukemia T-cells activated to transcribe NF-κB mediated gene transcription by phorbol myristate acetate (PMA) provide a new synthetically readily available scaffold for further optimization for cytokine inhibition in animals or humans in need thereof. In a further embodiment, $R_1$, $R_2$, and $R_3$ are moieties such that the compound inhibits a cyclin kinase, particularly wherein the cyclin kinase is GSK-3β or CDK-1. In a further embodiment, $R_1$, $R_2$, and $R_3$ are each independently selected from the group consisting of hydrogen, methyl, alkyl containing 1 to 6 carbon atoms, halo, aryl, acyl, hydroxyl, amine, thiol, ester, ether, and amide. It is further embodiment, it is preferable that $R_3$ is hydrogen. In a particularly preferred embodiment, the compound is compound 2.

Hymenialdisine and compound 2 were tested for inhibition of the checkpoint kinases Chk1 and CHK2 by UpState, Inc. Compound 2 inhibited Chk1 ($IC_{50}=237$ nM) and CHK2 ($IC_{50}=8$ nM) and was many folds more potent than the naturally-occurring hymenialdisines.

Thus, compounds which have the formula

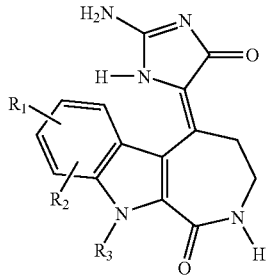

wherein $R_1$, $R_2$, and $R_3$ are moieties such that the compound inhibits checkpoint kinases provide a new synthetically readily available scaffold for further optimization for anticancer therapy in animals or humans in need thereof. In a further embodiment, $R_1$, $R_2$, and $R_3$ are each independently selected from the group consisting of hydrogen, methyl, alkyl containing 1 to 6 carbon atoms, halo, aryl, acyl, hydroxyl, amine, thiol, ester, ether, and amide. In a further embodiment, it is preferable that $R_3$ is hydrogen. In a particularly preferred embodiment, the compound is compound 2.

The present invention further provides a pharmaceutical composition which comprises one or more compounds according to the above formulae and a pharmaceutically acceptable carrier, diluent, or excipient. Thus, the compound may be used in the manufacture of a medicament. Pharmaceutical compositions of the compound synthesizes as described herein can be formulated as solutions or lyophilized powders for parenteral administration. The powders can be reconstituted by addition of a suitable diluent or other pharmaceutically acceptable carrier prior to use. The liquid formulation can be a buffered, isotonic, aqueous solution. Examples of suitable diluents are normal isotonic saline solution, standard 5% dextrose in water, or buffered sodium or ammonium acetate solution. Such formulations are especially suitable for parenteral administration, but may also be used for oral administration or contained in a metered dose inhaler or nebulizer for insulation. In particular embodiments, it can be desirable to further add one or more excipients selected from the group consisting of polyvinylpyrrolidone, gelatin, hydroxy cellulose, acacia, polyethylene glycol, mannitol, sodium chloride, and sodium citrate.

Alternately, one or more of the above compounds may be encapsulated, tableted or prepared in an emulsion or syrup for oral administration. Pharmaceutically acceptable solid or liquid carriers can be added to enhance or stabilize the composition, or to facilitate preparation of the composition. Solid carriers include starch, lactose, calcium sulfate dihydrate, terra alba, magnesium stearate or stearic acid, talc, pectin, acacia, agar, or gelatin. Liquid carriers include syrup, peanut oil, olive oil, saline, and water. The carrier can also include a sustained release material such as glyceryl monostearate or glyceryl distearate, alone or with a wax. The pharmaceutical preparations are made following the conventional techniques of pharmacy such as milling, mixing, granulating, and compressing, when necessary, for tablet forms; or milling, mixing, and filling for hard gelatin capsule forms. When a liquid carrier is used, the preparation will be in the form of a syrup, elixir, emulsion, or an aqueous or non-aqueous suspension. Such a liquid formulation can be administered directly or filled into a soft gelatin capsule.

For rectal administration, one or more of the above compounds can also be combined with excipients such as cocoa butter, glycerin, gelatin, or polyethylene glycols and molded into a suppository.

The methods of the present invention further include topical administration of one or more of the above compounds. By topical administration is meant non-systemic administration, including the application of a compound of the invention externally to the epidermis, to the buccal cavity, and instillation into the ear, eye, and nose, wherein the compound does not significantly enter the blood stream. By systemic administration is meant oral, intravenous, intraperitoneal, and intramuscular administration. The amount of a compound of the invention required for therapeutic or prophylactic effect upon topical administration will, of course, vary with the compound chosen, the nature and severity of the condition being treated and the animal or human undergoing treatment, and is ultimately at the discretion of the physician.

The topical formulations of the present invention, both for veterinary and for human medical use, comprise one or more of the above compounds together with one or more acceptable carriers therefor, and optionally any other therapeutic ingredients.

Formulations suitable for topical administration include liquid or semi-liquid preparations suitable for penetration through the skin to the site of where treatment is required such as: liniments, lotions, creams, ointments, or pastes, and drops suitable for administration to the eye, ear, or nose.

Drops according to the present invention may comprise sterile aqueous or oily solutions or suspensions and may be prepared by dissolving one or more of the above compounds in a suitable aqueous solution of a bactericidal and/or fungicidal agent and/or any other suitable preservative, and preferably including a surface active agent. The resulting solution can then be clarified by filtration, transferred to a suitable container which is then sealed and sterilized by autoclaving or maintaining at 90-100° C. for half an hour. Alternatively, the solution can be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion can comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments, or pastes according to the present invention are semi-solid formulations of the active ingredient for external application. They may be made by mixing the compound in finely-divided or powdered form, alone or in solution or suspension in an aqueous or non-aqueous fluid, with the aid of suitable machinery, with a greasy or non-greasy basis. The basis may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as propylene glycol or macrogols. The formulation may incorporate any suitable surface active agent such as an anionic, cationic or non-ionic surface active agent such as sorbitan esters or polyoxyethylene derivatives thereof. Suspending agents such as natural gums, cellulose derivatives or in organic materials such as silicaceous silicas, and other ingredients such as lanolin, may also be included.

The present invention also provides methods of treatment of diseases associated with NF-κB activation, which methods comprise administering to an animal, particularly an animal, most particularly a human in need thereof, one or more of the above compounds. The present invention particularly provides methods for treating inflammatory disorders; particularly rheumatoid arthritis, inflammatory bowel disease, and asthma; dermatosis, including psoriasis and atopic dennatitis; autoimmune diseases; tissue and organ rejection; Alzheimer's disease; stroke; atherosclerosis; restenosis; cancer, including Hodgkins disease; and certain viral infections, including AIDS; osteoarthritis; osteoporosis; and Ataxia Telangiectasia.

For acute therapy, parenteral administration of one or more of the above compounds is preferred. An intravenous infusion of the compound can be in 5% dextrose in water or normal saline, or a similar formulation with suitable excipients. Typically, the parenteral dose will be at a concentration effective to inhibit activation of NF-κB. The precise amount of an inventive compound which is therapeutically effective, and the route by which such compound is best administered, is readily determined by one of ordinary skill in the art by comparing the blood level of the agent to the concentration required to have a therapeutic effect.

The compounds of the above formula can also be administered orally to the animal or human, in a manner such that the concentration of drug is sufficient to inactivate NF-κB or to achieve any other therapeutic indication as disclosed herein. Typically, a pharmaceutical composition containing one or more of the above compounds is administered in amount which for the body weight of the animal or human inactivates the NF-κB.

One or more of the above compounds can also be administered topically to the animal or human, in a manner such that the concentration of drug is sufficient to inhibit NF-κB.

In some embodiments of the invention, the compound of the above formula is used in combination with one or more other anti-inflammatory, anti-viral, anti-fungal, amoebicidal, trichomonocidal, analgesic, anti-neoplastic, anti-hypertensives, anti-microbial and/or steroid drugs or potentiators. Such drugs include triprolidine or its cis-isomer which is used in combination with chemotherapeutic agents; a compound of the above formula and procodazole, 1H-benzimidazole-2-propanoic acid; [β-(2-benzimidazole) propionic acid 2-(2-carboxyethyl)benzimidazole; propazol] which is a non-specific immunoprotective agent active against viral and bacterial infections that is used with the compound of the above formula; or a compound of the above formula and a platinum-containing drug such as cisplatin which binds DNA which interferes with its DNA repair mechanism and thereby causing cellular death. Other drugs which can be used with a compound of the above formula, and optionally another chemotherapeutic agent, in the methods of the invention include macrophage colony-stimulating factor (M-CSF), 7-thia-8-oxoguanosine, 6-mercaptopurine, vitamin A (retinol), and other known anti-tumor potentiators which can be used in conjunction with the compounds of the above formula include, monensin, an anti-sense inhibitor of the RAD51 gene, bromodeoxyuridine, dipyridamole, indomethacin, a monoclonal antibody, an anti-transferrin receptor immunotoxin, metoclopramide, N-solanesyl-N,N'-bis(3,4-dimethoxybenzyl)ethylenediamine, leucovorin, heparin, N-[4-[(4-fluorphenyl)sulfonly]phenyl]acetamide, heparin sulfate, cimetidine, a radiosensitizer, a chemosensitizer, a hypoxic cell cytotoxic agent, muramyl dipeptide, vitamin A, 2'-deoxycoformycin, a bis-diketopiperazine derivative, and dimethyl sulfoxide other anti-tumor potentiators.

The chemotherapeutic agents which can be used with a compound of the above formula and an optional potentiator are generally grouped as DNA-interactive agents, antimetabolites, tubulin-interactive agents, hormonal agents, and others such as asparaginase or hydroxyarea. Each of the groups of chemotherapeutic agents can be further divided by type of activity or compound.

DNA-interactive agents include the alkylating agents, for example, cisplatin, cyclophosphamide, altretamine; the DNA strand-breaking agents, such as bleomycin; the intercalating topoisomerase II inhibitors, for example, dactinomycin and doxorubicin; the nonintercalating topoisomerase II inhibitors, such as etoposide and teniposide; and the DNA minor groove binder plicamycin.

The alkylating agents form covalent chemical adducts with cellular DNA, RNA, and protein molecules and with smaller amino acids, glutathione and similar chemicals. Generally, these alkylating agents react with a nucleophilic atom in a cellular constituent, such as an amino, carboxyl, phosphate, sulfhydryl group in nucleic acids, proteins, amino acids, or glutathione. The mechanism and the role of these alkylating agents in cancer therapy is not well understood. Typical alkylating agents include: nitrogen mustards, such as chlorambucil, cyclophosphamide, isofamide, mechlorethamine, melphalan, uracil mustard; aziridine such as thiotepa; methanesulphonate esters such as busulfan; nitroso ureas, such as carmustine, lomustine, streptozocin; platinum complexes, such as cisplatin, carboplatin; bioreductive alkylator, such as mitomycin, and procarbazine, dacarbazine, and altretamine.

DNA strand breaking agents include Bleomycin. DNA topoisomerase II inhibitors include the following: intercalators, such as amsacrine, dactinomycin, daunorubicin, doxorubicin, idarubicin, and mitoxantrone; and nonintercalators, such as etoposide and teniposide. The DNA minor groove binder is Plicamycin.

The antimetabolites interfere with the production of nucleic acids by one or the other of two major mechanisms. Some of the drugs inhibit production of the deoxyribonucleoside triphosphates that are the immediate precursors for DNA synthesis, thus inhibiting DNA replication. Some of the compounds are sufficiently like purines or pyrimidines to be able to substitute for them in the anabolic nucleotide pathways. These analogs can then be substituted into the DNA and RNA instead of their normal counterparts. The antimetabolites useful herein include: folate antagonists such as methotrexate and trimetrexate; pyrimidine antagonists, such as fluorouracil, fluorodeoxyunridine, CB3717, azacitidine and floxuridine; purine antagonists such as mercaptopurine, 6-thioguanine, pentostatin; sugar modified analogs such as cytarabine and fludarabine; and ribonucleotide reductase inhibitors such as hydroxyurea.

Tubulin interactive agents act by binding to specific sites on tubulin, a protein that polymerizes to form cellular microtubules. Microtubules are critical cell structure units. When the interactive agents bind on the protein, the cell can not form microtubules tubulin interactive agents include colchicine, vincristine and vinblastine, both alkaloids and paclitaxel and cytoxan.

Hormonal agents are also useful in the treatment of cancers and tumors. They are used in hormonally susceptible tumors and are usually derived from natural sources. These include estrogens, conjugated estrogens and ethinyl estradiol and diethylstilbesterol; chlortrianisen and idenestrol; progestins such as hydroxyprogesterone caproate medroxyprogesterone, and megestrol; and androgens such as testosterone, testosterone propionate, fluoxymesterone, and methyltestosterone.

Adrenal corticosteroids are derived from natural adrenal cortisol or hydrocortisone. They are used because of their anti inflammatory benefits as well as the ability of some to inhibit mitotic divisions and to halt DNA synthesis. These compounds include, prednisone, dexamethasone, methylprednisolone, and prednisolone.

Leutinizing hormone releasing hormone agents or gonadotropin-releasing hormone antagonists are used primarily the treatment of prostate cancer. These include leuprolide acetate and goserelin acetate. They prevent the biosynthesis of steroids in the testes.

Antihormonal antigens include: antiestrogenic agents such as tamoxifen; antiandrogen agents such as flutamide; and antiadrenal agents such as mitotane and aminoglutethimide.

Hydroxyurea, which appears to act primarily through inhibition of the enzyme ribonucleotide reductase, can also be used in combination with the compound of the above formula.

Asparaginase is an enzyme which converts asparagine to nonfunctional aspartic acid and thus blocks protein synthesis in the tumor. Asparaginase can also be used in combination with the compound of the above formula to treat cancer.

Other chemotherapeutic benzimidazoles and griseofulvin can also be used in combination with the compound of the above formula and optionally a potentiator to treat or inhibit the growth of cancer or extend the life span of a animal or human having cancer.

The amount and identity of a chemotherapeutic agent that is used with a compound of the above formula in the methods of the invention will vary according to cellular response, patient response and physiology, type and severity of side effects, the disease being treated, the preferred dosing regimen, patient prognosis, or other such factors.

The compound of the above formula can be used in combination with one or more other agents or combination of agents known to possess anti-leukemia activity including, by way of example, α-interferon; interleukin-2; cytarabine and mitoxantrone; cytarabine and daunorubicin and 6-thioguanine; cyclophosphamide and 2-chloro-2'-deoxyadenosine; VP-16 and cytarabine and idorubicin or mitoxantrone; fludarabine and cytarabine and γ-CSF; chlorambucil; cyclophosphamide and vincristine and (prednisolone or prednisone) and optionally doxorubicin; tyrosine kinase inhibitor; an antibody; glutamine; clofibric acid; all-trans retinoic acid; ginseng diyne analog; KRN8602 (anthracycline drug); temozolomide and poly(ADP-ribose) polymerase inhibitors; lysofylline; cytosine arabinoside; chlythorax and elemental enteral diet enriched with medium-chain triglycerides; amifostine; gilvusmycin; or a hot water extract of the bark of Acer nikoense.

The compounds of the above formula can further be administered to an animal or human with one or more imidazolines and optionally one or more of the above drugs or potentiators as a treatment for cellular proliferative diseases. As used herein, antiproliferative agents are compounds, which induce cytostasis or cytotoxicity. Cytostasis is the inhibition of cells from growing while cytotoxicity is defined as the killing of cells. Specific examples of antiproliferative agents include antimetabolites, such as methotrexate, 5-fluorouracil, gemcitabine, cytarabine; anti-tubulin protein agents such as the vinca alkaloids, paclitaxel, colchicine; hormone antagonists, such as tamoxifen, LHRH analogs; and nucleic acid damaging agents such as the alkylating agents melphalan, BCNU, CCNU, thiotepa, intercalating agents such as doxorubicin and metal coordination complexes such as cisplatin and carboplatin.

The following examples are intended to promote a further understanding of the present invention.

EXAMPLE 1

This example shows the synthesis of compounds 2 and 3 as shown in FIGS. 1B and 1C and Scheme 1.

Reactions were carried out in oven-dried glassware under nitrogen atmosphere, unless otherwise noted. All commercial reagents were used without further purification. All solvents were reagent grade. THF was freshly distilled from sodium/benzophenone under nitrogen. $CH_2Cl_2$ was freshly distilled from $CaH_2$ under nitrogen. All reactions were magnetically stirred and monitored by thin layer chromatography with Analtech 0.25-mm pre-coated silica gel plates (Analtech, Inc., Newark, Del.). Column chromatography was carried out on silica gel 60 (230-400 mesh) supplied by EM Science (END Chemicals, Inc., Gibbstown, N.J.). Yields refer to chromatographically and spectroscopically pure compounds unless otherwise stated. Infrared spectra were recorded on a Nicolet IR/42 spectrometer. Proton and carbon NMR spectra were recorded on a Varian Gemini-300 spectrometer or a Varian VXR-500 spectrometer (Varian Medical Systems, Inc., Palo Alto, Calif.). Chemical shifts were reported relative to the residue peaks of solvent chloroform ($\delta$ 7.24 for $^1H$ and $\delta$ 77.0 for $^{13}C$) and dimethyl sulfoxide ($\delta$ 2.49 for $^1H$ and $\delta$ 39.5 for $^{13}C$). High-resolution mass spectra were obtained at the Mass Spectrometry Laboratory of the University of South Carolina, Department of Chemistry & Biochemistry with a Micromass VG-70S mass spectrometer. Gas chromatography/low-resolution mass spectra were recorded on a Hewlett Packard 5890 Series II gas chromatograph connected to a TRIO-1 EI mass spectrometer. All regents were obtained from Aldrich Chemical Co., St. Louis, Mo., and used as received.

Synthesis of 3-[(1H-indole-2-carbonyl)-amino]-propionic acid ethyl ester, compound 4, was as follows. To a mixture of 2-indolecarboxylic acid (161 mg, 1.0 mmol), DMAP (200 mg, 6 mmol) and alanine ethyl ester hydrochloride (168 mg, 1.1 mmol) in 10 mL anhydrous $CH_2Cl_2$ was added EDCI (215 mg, 1.1 mmol) at 0° C. The mixture then was stirred at 0° C. for 4 hours and at room temperature for 20 hours. The mixture was washed with water (20 mL) and 10% HCl (10 mL), dried over anhydrous $Na_2SO_4$, filtered, and concentrated to yield product 4 as a white solid (230 mg, 88.5%). Mp 158-160° C. $^1H$ NMR: (300 MHz, $CDCl_3$) $\delta$ 1.28 (t, 3H, J=7.2 Hz), 2.69 (t, 2H, J=5.7 Hz), 3.78 (q, 2H, J=6.0 Hz), 4.18 (q, 2H, J=6.9, 7.2 Hz), 6.89 (s, 1H), 7.05 (s, 1H), 7.13-7.68 (m, 4H), 9.86 (s, 1H). $^{13}C$ NMR: (74.47 MHz, $CDCl_3$) $\delta$ 14.1, 33.9, 34.9, 60.8, 102.2, 111.9, 120.4, 121.8, 124.3, 127.5, 130.5, 136.4, 161.7, 172.8. IR: (NaCl) 3377, 3352, 1716, 1624, 1551, 1325, 1207, 748 cm$^{-1}$. HRMS m/e calcd for $C_{14}H_{16}N_2O_3$ (M) 260.1161, found 260.1159.

Synthesis of 3-[(1-methyl-1H-indole-2-carbonyl)-amino]-propionic acid ethyl ester, compound 5, was as follows. A solution of compound 4 (0.5 g, 1.9 mmol), $K_2CO_3$ (1.06 g, 7.68 mmol) and iodomethane (0.29 mL, 4.64 mmol) in acetonitrile (15 mL) was stirred at reflux for 24 hours. The mixture was cooled, filtered and the filtrate was evaporated in vacuo. The crude material was further purified by column chromatography on silica gel ($CH_2Cl_2$—AcOEt 3:1) to yield compound 5 as white solid (512 mg, 98%); Mp 75-77° C. $^1H$ NMR: (300 MHz, $CDCl_3$) $\delta$ 1.28 (t, 3H, J=7.2 Hz), 2.67 (m, 2H), 3.72 (m, 2H), 4.07 (s, 3H), 4.22 (q, 2H, J=6.9 Hz), 6.86 (s, 1H), 7.05-7.65 (m, 4H). $^{13}C$ NMR: (74.47 MHz, $CDCl_3$) $\delta$ 14.1, 31.4, 33.9, 34.8, 60.7, 103.8, 110.1, 120.3, 121.7, 123.9, 125.9, 131.8, 138.9, 162.4, 172.6. IR (NaCl): 3263, 1732, 1630, 1552, 1462, 1392, 1321, 1182, 746 cm$^{-1}$. HRMS m/e calcd for $C_{15}H_{18}N_2O_3$ (M) 274.1317, found 274.1315.

Synthesis of 3-[(1-methyl-1H-indole-2-carbonyl)-amino]-propionic acid, compound 7, was as follows. A solution of compound 5 (420 mg, 1.53 mmol) and LiOH (129 mg, 3.07 mmol) in ethanol (14 mL) was stirred at room temperature for 18 hours. After cooling, the solvent was evaporated in vacuo. The residue was dissolved in water and acidified with 1N HCL to pH=3 to afford white precipitate, which isolated by filtration and washed with water to provide compound 7 (360 mg, 95%); Mp 160-162° C. $^1H$ NMR: (300 MHz, d$^6$-DMSO) $\delta$ 2.49 (t, 2H, J=7.2 Hz), 3.46 (q, 2H, J=6.6 Hz), 3.97 (s, 3H), 7.07-7.64 (m, 5H), 8.54 (t, 1H, J=5.7 Hz). $^{13}C$ NMR: (74.47 MHz, d$^6$-DMSO) $\delta$ 31.3, 33.8, 35.2, 104.3, 110.5, 120.1, 121.5, 123.5, 125.6, 132.1, 138.4, 161.9, 173.0. IR (NaCl): 3385, 2966, 1713, 1603, 1550, 1468, 1425, 1400, 1282, 1228, 1192, 910, 748 cm$^{-1}$. HRMS m/e calcd for $C_{13}H_{14}N_2O_3$ (M) 246.1004, found 246.1016.

Synthesis of 10-methyl-3,4-dihydro-2H,10H-azepino[3,4-b]indole-1,5-dione, compound 9, was as follows. Compound 7 (2.16 g, 8.78 mmol) was added to a clear solution of $P_2O_5$ (3.49 g, 12.3 mmol) in $MeSO_3H$ (21 mL) at 60° C. The mixture was heated to 110° C. for 1 hour, after which the mixture was cooled to room temperature. The reaction mixture was poured into ice-water, stirred for 30 minutes, filtered and washed with water, to provide compound 9 (1.143 g) as a solid (57%). Mp 200-205° C. $^1H$ NMR: (500 MHz, d$^6$-DMSO) $\delta$ 2.77 (t, 2H, J=5.5 Hz), 3.39 (t, 2H, J=5.5, 4.5 Hz), 3.99 (s, 3H), 7.27 (t, 1H, J=7.0, 8.0 Hz), 7.37 (t, 1H, J=7.5 Hz), 7.62 (d, 1H, J=8.0 Hz), 8.27 (d, 1H, J=8.0 Hz), 8.77 (t, 1H, J=5.0, 6.0 Hz); $^{13}C$ NMR: (124.1 MHz, d$^6$-DMSO) $\delta$ 33.0, 37.3, 45.6, 111.6, 115.5, 123.4, 123.8, 125.3, 125.7, 135.4, 138.7, 163.1, 196.4. IR (NaCl): 3204, 3000, 2924, 1662, 1641, 1506, 1473, 1371, 724 cm$^{-1}$; HRMS m/e calcd for $C_{13}H_{12}N_2O_2$ (M) 228.0899, found 228.0887.

Synthesis of 10-methyl-5-(5-oxo-2-phenyl-oxazol-4-ylidene)-3,4,5,10-tetrahydro-2H-azepino[3,4-b]indol-1-one, compound 11 was as follows. A solution of $TiCl_4$ (1.54 mL, 14 mmol) in $CH_2Cl_2$ (10 mL) was added into THF (10 mL) at 0° C. Compound 9 (802 mg, 3.5 mmol) and 2-phenylazlactone (1.13 g, 7 mmol) were added to this mixture. The mixture was stirred at 0° C. for 20 minutes after which pyridine (1.13 mL, 14 mmol) was added. The reaction mixture was stirred at 0° C. for an additional 2 hours, after which it was allowed to stir overnight at room temperature. $NH_4Cl$ (80 mL, sat. solution in water) was added and the mixture was stirred for 10 minutes. The mixture was subsequently extracted with ethyl acetate (3 times), the extracts combined, dried with anhydrous $Na_2SO_4$, filtered, concentrated and the residue was purified with column chromatography on silica gel (ethyl acetate-hexane 8:2) to yield compound 11 (0.73 g, 56%) as yellow solid. Mp: 189-192° C. $^1H$ NMR: (300 MHz, $CDCl_3$) $\delta$ 3.54 (t, 2H, J=3.3, 3.6 Hz), 3.59 (t, 2H, J=2.7, 3.3 Hz), 4.09 (s, 3H), 6.94 (s, 1H), 7.24-7.27 (m, 1H), 7.38-7.49 (m, 5H), 7.78 (d, 1H, J=4.8 Hz), 7.92 (d, 2H, J=6.0 Hz); $^{13}C$ NMR:

(74.47 MHz, CDCl$_3$) δ 31.9, 38.2, 38.4, 110.1, 115.8, 121.3, 124.3, 125.0, 125.1, 125.8, 127.5, 128.7, 130.0, 131.7, 132.4, 138.5, 144.5, 159.4, 165.3, 165.9. IR: (NaCl) 1784, 1753, 1662, 1633, 1473 cm$^{-1}$; LRMS (EI): 371.1 (M); HRMS m/e calcd for C$_{22}$H$_{17}$N$_3$O$_3$ (M) 371.1270, found 371.1268.

Synthesis of 5-(2-amino-5-oxo-1,5-dihydro-imidazol-4-ylidene)-10-methyl-3,4,5,10-tetrahydro-2H-azepino[3,4-b]indol-1-one, compound 3, was as follows. LiH (48 mg, 6 mmol) was dissolved in ethanol (150 mL) and to this solution was added compound 11 (371 mg, 1.0 mmol) and S-benzyl-isothiouronium chloride (1.01 g, 5 mmol). The reaction was refluxed 48 hours, after which the solvent was evaporated in vacuo. 50 mL ethanol was added to the reaction and was evaporated. This was repeated 3 times. Ethanol (15 mL) was added again and the reaction was refluxed for 3 hours, after which the solvent was distilled off in vacuum. 1N HCL$_{(aq)}$ (50 mL) was added and the product was extracted with n-butanol (3×50 mL). The extracts were combined and washed with brine (3×20 mL), dried, concentrated and the product was purified by column chromatography on silica gel (CH$_2$Cl$_2$: MeOH: NH$_3$.H$_2$O, 3:1:0.1) to yield compound 3 as light yellow solid (96 mg, 31%) Mp: >260° C. $^1$H NMR: (300 MHz, d$^6$-DMSO) δ 2.99-3.48 (m, 4H) 3.92 (s, 3H), 7.19 (t, 1H, J=7.2 Hz), 7.36 (t, 1H, J=6.6 Hz), 7.55 (d, 1H, J=8.1 Hz), 7.65 (d, 1H, J=8.4 Hz), 8.57 (t, 1H, J=5.1 Hz), 9.15-9.25 (br-s, 1H), 10.48 (s, 1H); $^{13}$C NMR: (74.47 MHz, d$^6$-DMSO) δ 32.1, 37.1, 38.4, 111.7, 112.6, 122.1, 122.2, 123.5, 123.7, 125.1, 128.1, 132.8, 138.5, 154.6, 163.0, 165.1; IR: (KBr-pellet) 3211, 1699, 1635, 1508, 1477 cm$^{-1}$; LRMS (EI): 308.7 (M); HRMS m/e calcd for C$_{16}$H$_{15}$N$_5$O$_2$ (M) 309.1304, found 309.1291.

Synthesis of 3-[(1H-indole-2-carbonyl)-amino]-propionic acid ethyl ester, compound 6, was as follows. A mixture of compound 4 (1.838 g, 7.38 mmol) and LiOH (0.6 g, 14.1 mmol) was stirred at room temperature in ethanol (50 mL) for 20 hours, the ethanol was evaporated to dryness in vacuo. The residue was dissolved in water (50 mL), acidified the solution to pH=1 with HCL (aq), at which a white solid precipitated. The mixture was allowed to stand at 0° C. for 30 minutes, after which the product was filtered of, dried in vacuum, to yield compound 6 (1.45 g, 84%). Mp 232° C. $^1$H NMR: (300 MHz, d$^6$-DMSO) δ 2.52 (t. 2H, J=6.9 Hz), 3.47 (q, 2H, J=6.6, 6.0 Hz), 6.98 (t, 1H, J=7.2 Hz), 7.10 (s, 1H), 7.13 (t, 1H, J=7.2 Hz), 7.41 (1H, J=8.1 Hz), 7.57 (1H, J=8.1 Hz), 8.52 (s, 1H), 11.55 (s, 1H), 12.25 (s, 1H); $^{13}$C NMR: (74.47 MHz) (d$^6$-DMSO) δ 34.6, 35.9, 103.2, 112.9, 120.3, 122.1, 123.9, 127.8, 132.4, 137.1, 161.8, 173.4; IR (NaCl): 3422, 3273, 1745, 1707, 1643, 1549, 1417, 1341, 1259, 746 cm$^{-1}$; HRMS m/e calcd for C$_{12}$H$_{12}$N$_2$O$_3$ (M) 232.0848, found 232.0844.

Synthesis of 3,4-dihydro-2H,10H-azepino[3,4-b]indol-1,5-dione, compound 8, was as follows. Compound 6 (116 mg, 0.5 mmol) was added to a clear solution of P$_2$O$_5$ (232 mg, 0.8 mmol) in MeSO$_3$H (1.57 mL) at 60° C. The mixture was heated to 110° C. for 1.5 hour, after which the mixture was cooled to room temperature. The reaction mixture was poured into ice-water, stirred for 30 minutes, filtered, dissolved in acetone (100 mL), filtered again, and the filtrate was concentrated. The product was further purified by column chromatography on silica gel to yield compound 8 (88 mg, 82%) Mp: 257-260° C. $^1$H NMR (300 MHz, d$^6$-DMSO) δ 2.80-2.85 (m, 2H), 3.40-3.46 (m, 2H), 7.22-7.38 (m, 2H), 7.51 (d, 1H, J=9.0 Hz), 8.28 (d, 1H, J=9 Hz), 8.72 (m, 1H), 12.41 (s, 1H); $^{13}$C NMR (74.47 MHz, d$^6$-DMSO) δ 36.7, 44.2, 112.7, 113.8, 122.8, 122.9, 125.0, 126.2, 134.7, 135.7, 162.5, 195.3; IR: (KBr-pellet) 3209, 1664, 1630, 1523, 1437, 1408 cm$^{-1}$; LRMS (EI): M$^+$=214.3; HRMS m/e calcd for C$_{12}$H$_{10}$N$_2$O$_2$ (M) 214.0742, found 214.0740.

Synthesis of 5-(5-oxo-2-phenyl-oxazol-4-ylidene)-3,4,5,10-tetrahydro-2H-azepino[3,4-b]indol-1-one, compound 10, was as follows. A solution of TiCl$_4$ (132 µL, 1.2 mmol) in CH$_2$Cl$_2$ (1.2 mL) and the mixture was added into THF (3 mL) at 0° C. Compound 8 (65 mg, 0.3 mmol) and 2-phenylazlactone (97 mg, 0.6 mmol) were subsequently added to this mixture. The reaction mixture was stirred at 0° C. for an additional 2 hours, after which it was allowed to stir overnight at room temperature. NH$_4$Cl (8 mL, sat. solution in water) was added and the mixture was stirred for 10 minutes. The mixture was subsequently extracted with ethyl acetate (3 times), the extracts combined, dried with anhydrous Na$_2$SO$_4$, filtered, concentrated and the residue was purified with column chromatography on silica gel (acetone) to yield compound 10 (59 mg, 55%) as a foamy yellow solid. Mp: 247-250° C. $^1$H NMR (300 MHz, d$^6$-DMSO) δ 3.36-3.47 (m, 4H), 7.14 (t, 1H, J=8.1 Hz), 7.30 (t, 1H, J=9.0 Hz), 7.49-7.58 (m, 4H), 7.81-7.87 (m, 3H), 8.45-8.56 (m, 1H), 12.11 (s, 1H); $^{13}$C NMR (74.47 MHz, d$^6$-DMSO) δ 37.7, 38.6, 112.9, 115.3, 121.0, 125.1, 125.3, 126.5, 127.4, 129.0, 129.8, 133.2, 134.0, 136.9, 146.3, 158.4, 165.0, 166.1; IR: (KBr-pellet) 3358, 3179, 1749, 1653, 1633, 1448 cm$^{-1}$; HRMS m/e calcd for C$_{21}$H$_{15}$N$_3$O$_3$ (M) 357.1113, found 357.1106.

Synthesis of 5-(2-amino-5-oxo-1,5-dihydro-imidazol-4-ylidene)-3,4,5,10-tetrahydro-2H-azepino[3,4-b]indol-1-one, compound 2, was as follows. LiH (16 mg, 2 mmol) was dissolved in ethanol (60 mL) and to this solution was added compound 10 (150 mg, 0.4 mmol) and S-benzylisothiouronium chloride (405 mg, 2 mmol). The reaction was refluxed 48 hours after which the reaction was cooled and the solvent was evaporated in vacuo. Ethanol (20 mL) added and subsequently evaporated 3 times. Ethanol (5 mL) was added again and the reaction was refluxed for 3 hours. The solvent was evaporated off in vacuum, 1N HCl$_{(aq)}$ (15 mL) was added and the mixture was extracted with n-butanol (3×15 mL), the extracts were washed with brine (3×10 mL), dried, concentrated and the product was purified by column chromatography on silica gel (CH$_2$Cl$_2$:MeOH:NH$_3$.H$_2$O, 3:1:0.1) to yield compound 2 (35 mg, 30%) as light yellow solid, Mp: >260° C.; $^1$H NMR (300 MHz, d$^6$-DMSO) δ 3.20-3.40 (br., 4H), 7.16 (t, 1H, J=12.0 Hz), 7.29 (t, 1H, J=12.0 Hz), 7.52 (m, 2H), 8.30-8.50 (m, 2H), 9.05-9.25 (br.), 1H), 10.30-10.40 (m, 1H), 12.48 (s, 1H); $^{13}$C NMR: (124.1 MHz), d$^6$-DMSO) δ 36.5, 39.2, 112.7, 113.5, 121.9, 122.3, 122.8, 124.5, 125.0, 128.6, 132.8, 137.0, 154.6, 163.4, 165.5; IR: (KBr-pellet) 3294, 1620, 1475, 1251 cm$^{-1}$; LRMS (EI): 295.1 (M); HRMS (FAB) calcd for C$_{15}$H$_{14}$N$_5$O$_2$ (M+H) 296.1148, found 296.1144.

EXAMPLE 2

This example shows that compound 2, like hymeniadisine 1, exhibits a significant dose response inhibition of IL-2 production when measured in a competitive enzyme immunoassay (EIA) for IL-2 expression.

Human Jurkat leukemia T-cells (clone E6-1; ATCC No. TIB-152, American Type Culture Collection, 10801 University Boulevard, Manassas, Va.) are grown in RPMI-1640 Media (Gibco-BRL, Rockville, Md.) supplemented with 10% fetal bovine serum, penicillin (614 ng/mL), streptomycin (10 µg/mL) and HEPES buffer, pH 7.2 at 37° C., 5% CO$_2$. To each well of a flat bottomed 96 well culture plate 0.2 mL 1×10$^6$ Jurkat E6-1 cells/mL were added. Each sample was then treated in duplicate with the compounds in DMSO at either 10 µM, 1 µM, 0.1 µM or 10 nM and allowed to incubate for thirty minutes at 37° C., 5% CO$_2$. Cell free supernatant fractions were collected from stimulated cultures incubated for 24 hr at 37° C., 5% $CO_2$. Cultures were stimulated with phytohemagglutinin (PHA, Sigma-Aldrich, St. Louis, Mo.) at 1 µg/mL; and phorbol myristate acetate (PMA, Sigma-Aldrich, St. Louis, Mo.) at 50 ng/mL. The concentration of IL-2 in each sample was then measured using a competitive enzyme immunoassay (Neogen Corporation, Lansing, Mich.) according to the manufacturer's protocol. Known IL-2 concentrations were plotted and fit a 4 parameter logistic curve. Unknown concentrations were then extrapolated from the standard curve.

Figure 2A:
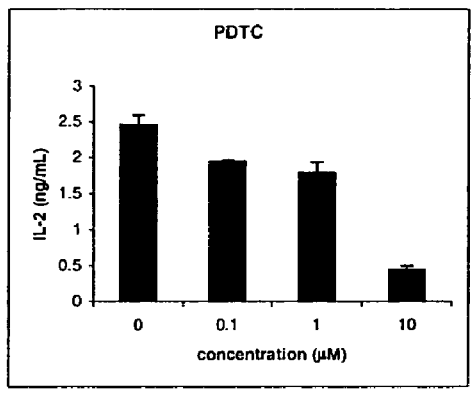
FIG. 2A shows IL-2 production as measured by ELISA with PDTC.
Figure 2B:
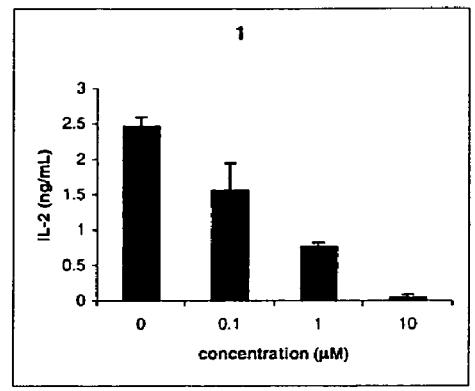
FIG. 2B shows IL-2 production as measured by ELISA with hymenialdisine 1.
Figure 2C:
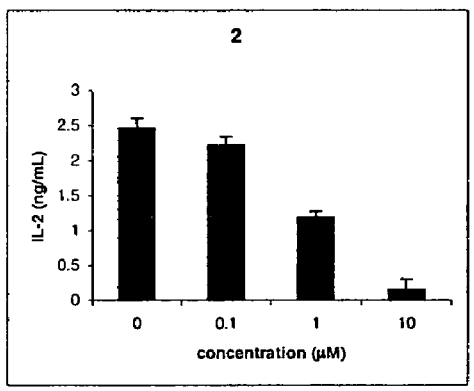
FIG. 2C shows IL-2 production as measured by ELISA with chemically-synthesized indoloazepine compound 2.

Hymenialdisine 1 exhibited significant inhibition of IL-2 production with an $IC_{50}$ value of 2.4 µM (Table 1 and FIG. 2B). Treatment of the Jurkat cells with compound 2 at concentrations ranging from 0.1 µM to 10 µM exhibited also a significant dose response inhibition of IL-2 production (FIG. 2C). Compound 2 exhibited an inhibition of IL-2 production with an $IC_{50}$ value of 3.5 µM.

Figure 2D:
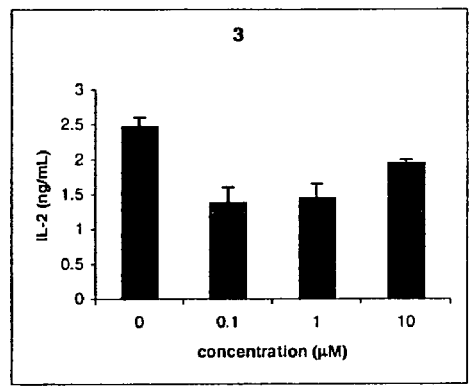
FIG. 2D shows IL-2 production as measured by ELISA with chemically-synthesized indoloazepine compound 3.

Interestingly, blockage of the N-indole position with a methyl group, compound 3, indicated no significant inhibition of IL-2 production up to the concentration tested (FIG. 2D, measured up to 10 µM). This further supports the significance of the pyrrolic —H-moiety in potential hydrogen bonding interactions (Meijer et al., Chem. Biol. 7: 51-63 (2000)). FIG. 2A shows the effect of PDTC on the cells.

TABLE 1

Inhibition of IL-2 production measured by EIA for PDTC, hymenialdisine 1 and compounds 2 and 3 in PMA/PHA-activated Jurkat T cells.

| Compounds | Inhibition of IL-2 Production $IC_{50}$, (µM)[a] |
| --- | --- |
| PDTC (control) | 5.123 (±0.407) |
| Hymenialdisine 1 | 2.411 (±0.710) |
| Compound 2 | 3.547 (±0.092) |
| Compound 3 | >10 |

[a]Values are means of two experiments, standard deviation is given in parentheses.

EXAMPLE 3

This example shows that compound 2, like hymeniadisine 1, exhibits a significant inhibition of NF-κB-DNA binding when measured in an EMSA assay for NF-κB-DNA binding in which the nuclear extracts of PMA/PHA activated Jurkat cells were examined for inhibition of DNA binding of NF-κB by compounds 1-3 using gel electrophoresis (EMSA).

Human Jurkat leukemia T-cells (clone E6-1; ATCC No. TIB-152, American Type Culture Collection, 10801 University Boulevard, Manassas, Va.) are grown in RPMI-1640 Media (Gibco-BRL, Rockville, Md.) supplemented with 10% fetal bovine serum, penicillin (614 n/mL), streptomycin (10 µg/mL) and HEPES buffer, pH 7.2 at 37° C., 5% $CO_2$. The Jurkat cells ($1 \times 10^6$ cells/mL) are subsequently treated with various concentrations of the compounds in DMSO for 30 min. at 37° C. and 5% $CO_2$ followed by PMA (50 ng/mL) and PHA (1 µM/mL) stimulation for an additional 30 minutes. The cells were harvested by centrifugation, washed in ice cold PBS and the nuclear extracts were prepared as previously described (Dignam et al., Nucl. Acids Res. 11: 1475-1489 (1983)). The protein concentration of the extracts was determined according to the Method of Bradford (1976) with BioRad reagents.

Nuclear extracts were incubated for 20 minutes at room temperature with a double stranded Cy3 labeled NF-κB consensus oligonucleotide, 5'-AGTTGAGGGGACTTTCCCAGGC-3' (SEQ ID NO:1). The binding mixture (25 µL) contained 10 mM HEPES-NaOH pH 7.9, 4 mM Tris-HCL, pH 7.9, 6.0 mM KCl, 1 mM EDTA, 1 mM DTT, 10% glycerol, 0.3 mg/mL bovine serum albumin, and 1 µg of poly (dI:dC). The binding mixtures (10 µg of nuclear extract protein) were incubated for 20 minutes at room temperature with 0.16 pmol of Cy3 labeled oligonucleotide. The mixture was loaded on a 4% polyacrylamide gel prepared in 1×TRIS borate/EDTA buffer and was electrophoresed at 200 V for 20 minutes. After electrophoresis the gel was analyzed using a phosphorimager (BIORAD FX PLUS, Biorad Laboratories, Inc., Hercules, Calif.) for detection of NF-κB-DNA binding.

Figure 3:
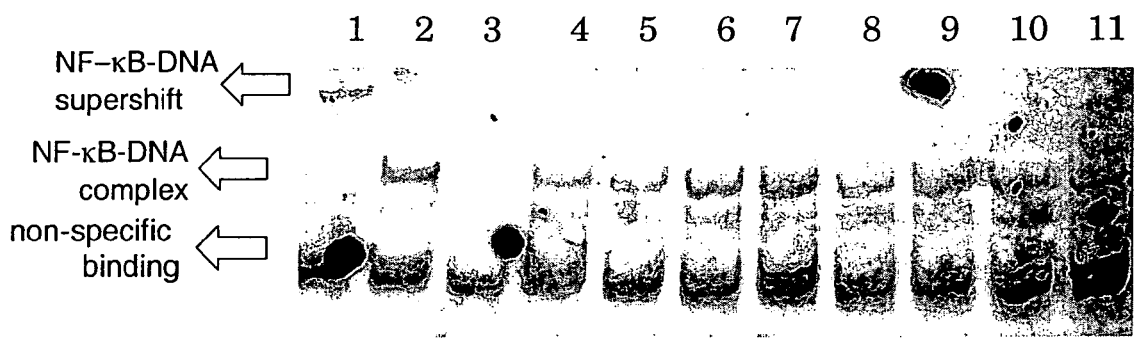
FIG. 3 shows EMSA assays for NF-κB-DNA binding inhibition by compounds 1-3. Lane 1: NF-κB consensus oligo (0.16 pmol/λ)+nuclear extract (+PMA/PHA)+Antibody p65; Lane 2: NF-κB consensus oligo (0.16 pmol/λ)+nuclear extract (PMA/PHA); Lane 3: NF-κB consensus oligo (0.16 pmol/λ)+nuclear extract (—PMA/–PHA); Lane 4: NF-κB consensus oligo (0.16 pmol/λ)+nuclear extract (PMA/PHA)+5 μM PDTC; Lane 5: NF-κB consensus oligo (0.16 pmol/λ)+nuclear extract (PMA/PHA)+1 μM PDTC; Lane 6: NF-κB consensus oligo (0.16 pmol/λ)+nuclear extract (PMA/PHA)+5 μM compound 1; Lane 7: NF-κB consensus oligo (0.16 pmol/λ)+nuclear extract (PMA/PHA)+1 μM compound 1; Lane 8: NF-κB consensus oligo (0.16 pmol/λ)+ nuclear extract (PMA/PHA)+5 μM compound 2; Lane 9: NF-κB consensus oligo (0.16 pmol/λ)+nuclear extract (PMA/PHA)+1 μM compound 2; Lane 10: NF-κB consensus oligo (0.16 pmol/λ)+nuclear extract (PMA/PHA)+5 μM compound 3; Lane 11: NF-κB consensus oligo (0.16 pmol/λ)+nuclear extract (PMA/PHA)+1 μM compound 3.

The results are shown in FIG. 3 and Table 2. Control lanes included lane 1, in which the NF-κB p65 antibody was used to confirm the NF-κB-DNA complex (FIG. 3). Addition of the antibody to the nuclear extract of activated Jurkat cells resulted in a supershift indicated in FIG. 3 (lane 1). The DNA-NF-κB complex is illustrated in lane 2. Lane 3 includes the DNA binding of a non stimulated cell extract, which as anticipated resulted in no significant band shift (lane 3). Lanes 4 and 5, were treated with 5 µM and 1 µM PDTC, respectively as a positive control for NF-κB-DNA binding inhibition.

Inhibition of NF-κB-DNA binding was found to be 51% and 30% for 5 µM and 1 µM PDTC, respectively (lanes 4 and 5) as compared to the activated control (lane 2). Hymenialdisine at 5 µM (46% inhibition) and 1 µM concentration (3% inhibition, lanes 6 and 7, respectively) indicated significant inhibition of DNA binding as reported earlier (Roshak et al., J. Pharmacol. Exp. Ther. 283: 955-961 (1997)). Compound 2, demonstrated similar inhibition of NF-κB-DNA binding as the natural product hymenialdisine with 49% and 22% inhibition at 5 µM and 1 µM, respectively (lanes 8 and 9). Compound 3 did not appear to substantially inhibit DNA binding as measured up to concentrations of 5 µM (lanes 10 and 11). In fact, a small increase in binding was observed as compared to the activated control. A summary of the percent inhibition relative to the activated control is listed in Table 3. Similar to the studies reported on hymenialdisine (Roshak et al., J. Pharmacol. Exp. Ther. 283: 955-961 (1997)), no significant inhibition of DNA binding was observed when compounds 1-3 were tested for inhibition of DNA binding with the transcription factor AP-1.

TABLE 2

Inhibition of NF-κB-DNA binding measured by EMSA for PDTC, hymenialdisine 1 and compounds 2 and 3 in PMA-activated Jurkat cells.

| Compounds | Inhibition of DNA-binding (relative to activated control) | Count per $mm^2$ NF-κB bands |
| --- | --- | --- |
| Activated cells (control) | — | 105.55 |
| 5.0 µM PDTC (control) | 51% | 51.68 |
| 1.0 µM PDTC (control) | 30% | 73.48 |
| 5.0 µM Hymenialdisine 1 | 46% | 57.06 |
| 1.0 µM Hymenialdisine 1 | 3% | 102.14 |
| 5.0 µM Compound 2 | 49% | 53.40 |
| 1.0 µM Compound 2 | 22% | 82.38 |
| 5.0 µM Compound 3 | 0% | 121.76 |
| 1.0 µM Compound 3 | 0% | 118.82 |

EXAMPLE 4

This example shows that compound 2, like hymenialdisine 1, exhibits a significant dose response inhibition of TNF-α when measured in a competitive enzyme immunoassay (EIA) for TNF-α expression. The assay measured the ability of the compounds to inhibit TNF-α production in LPS stimulated THP-1 cells (Aikawa et al., Inflamm. Res. 51V 188-194 (2002)).

THP-1 cells are grown in RPMI-1640 Media (Gibco-BRL, Rockville, Md.) supplemented with 5% fetal bovine serum, penicillin (614 ng/mL), streptomycin (10 μg/mL) and HEPES buffer, pH 7.2 at 37° C., 5% $CO_2$. To each well of a flat bottomed 96 well culture plate 0.2 mL $1 \times 10^6$ THP-1 cells/mL were added. Each sample was then treated in duplicate with the compounds in DMSO at either 10 μM, 1 μM, 0.1 μM or 10 nM and allowed to incubate for thirty minutes at 37° C., 5% $CO_2$. Cell free supernatant fractions were collected from stimulated cultures incubated for 3 hr at 37° C., 5% $CO_2$. Cultures were stimulated with LPS (Sigma-Aldrich, St. Louis, Mo.) at 1 μg/mL. The concentration of TNF-α in each sample was then measured using a competitive enzyme immunoassay (Neogen Corporation, Lansing, Mich.) according to the manufacturer's protocol. To make a standard curve, known TNF-α concentrations were plotted and fitted to a 4 parameter logistic curve. Unknown concentrations were then extrapolated from the standard curve.

Figure 5:
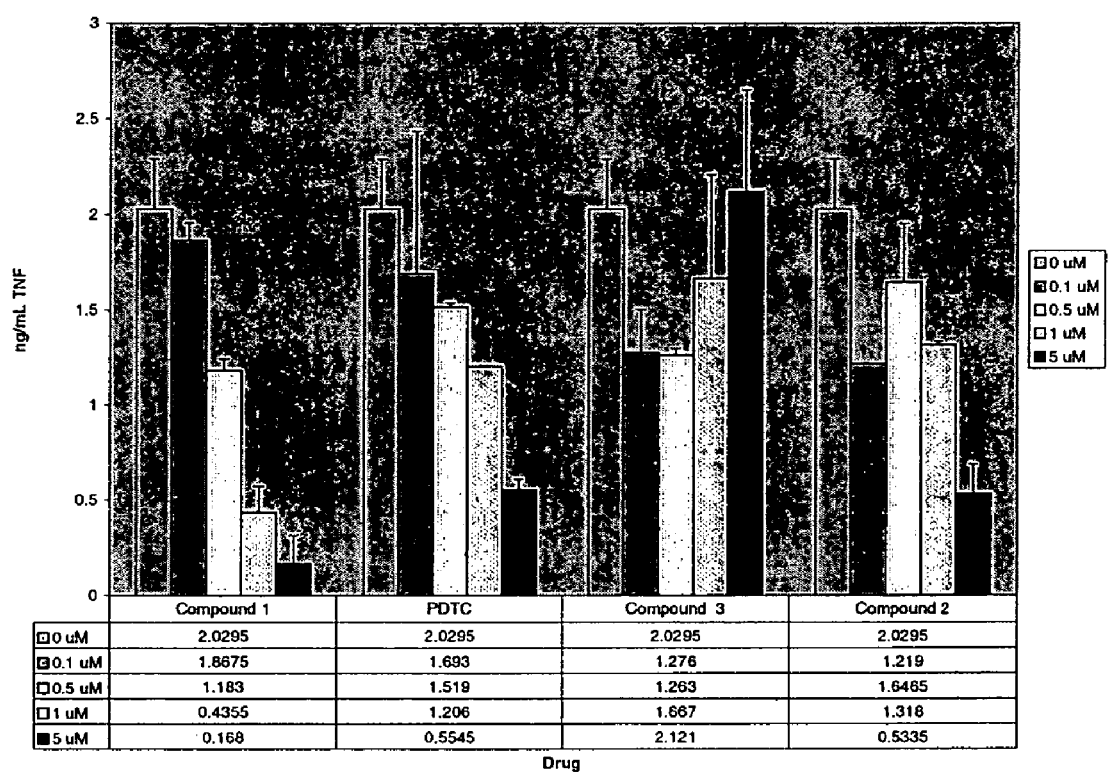
FIG. 5 is a chart which compares the effect of compounds 1-3 on TNF-α production in THP-1 cells after stimulation with LPS.

Treatment of THP-1 cells with PDTC and compounds 1-3, 30 minutes prior to LPS activation, resulted in a significant inhibition of TNF-α production after a 3 hour incubation period (Table 3 and FIG. 5). Hymenialdisine 1 was found to be a potent inhibitor of TNF-α production with an $IC_{50}$ value of 1.4 μM. Compound 2 was also found to inhibit TNF-α production, albeit less potent than hymenialdisine ($IC_{50}$=8.2 μM). The methylated indoloazepine 3 did not have any significant activity at the concentrations tested (tested up to 10 μM, Table 3).

TABLE 3

Inhibition of TNF-α production measured by EIA for PDTC, hymenialdisine 1 and compounds 2 and 3 in PMA/PHA-activated THP-1 cells.

| Compounds | Inhibition of TNF-α Production $IC_{50}$, (μM)[a] |
|---|---|
| PDTC (control) | 6.109 (±0.529) |
| Hymenialdisine 1 | 1.357 (±0.253) |
| Compound 2 | 8.161 (±0.313) |
| Compound 3 | >10 |

[a]Values are means of two experiments, standard deviation is given in parentheses.

EXAMPLE 5

Hymenialdisine 1 and compounds 2 and 3 were tested for their cytotoxicity and were found to exhibit significant inhibition of cell growth. Cells were treated at different concentrations ranging from 10 nM to 5 μM concentrations over a 48 hour time period.

Figure 6A:
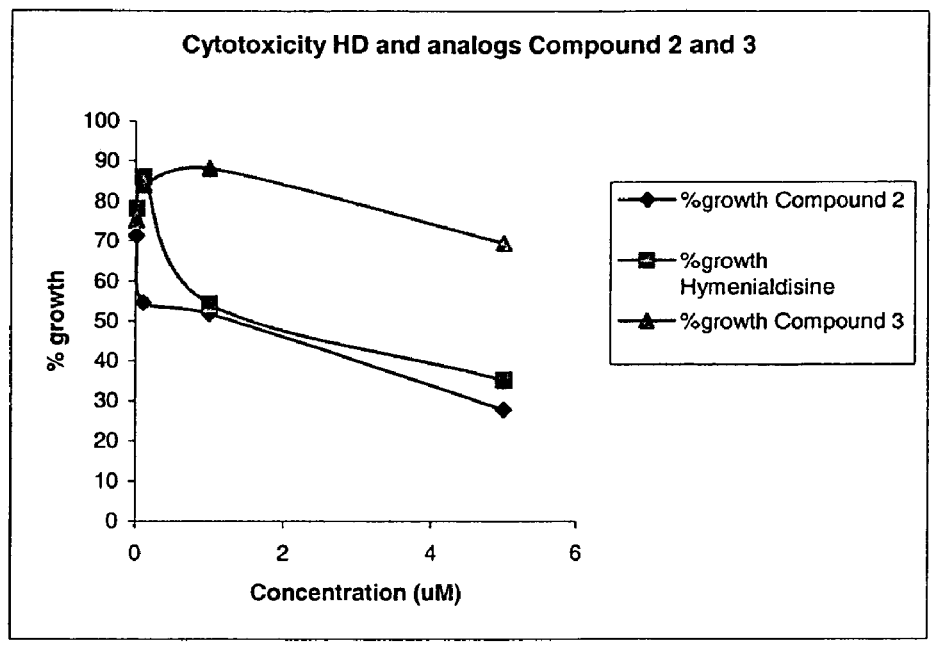
FIG. 6A compares the cytotoxicity of hymenialdisine to compounds 2 and 3. Number of cells were normalized on a scale of 100.
Figure 6B:
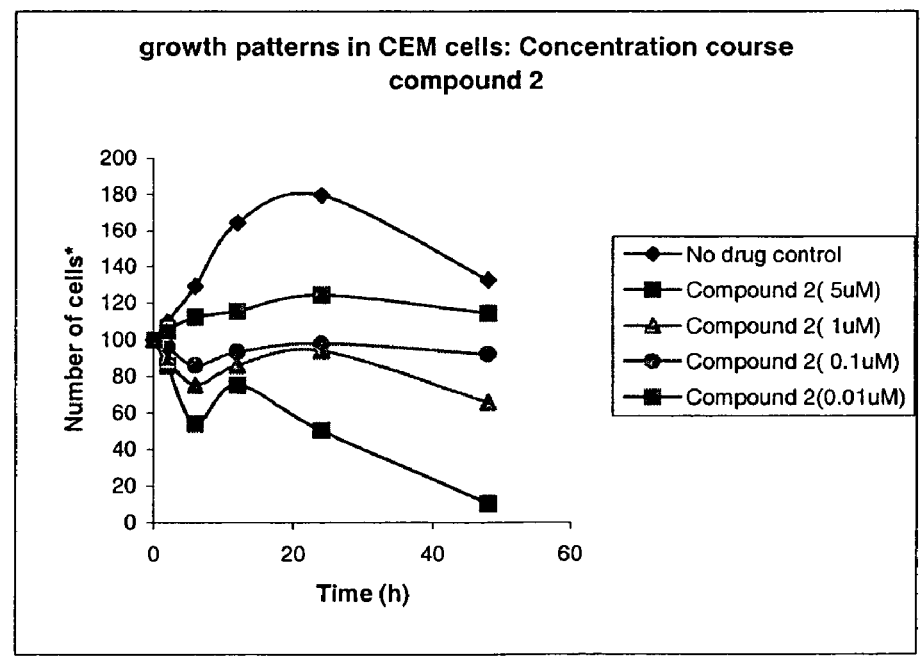
FIG. 6B shows the growth patterns in CEM cells at different concentrations of compound 2. Number of cells were normalized on a scale of 100.

CEM cells (CCRF-CEM; ATCC No. CCL-119, American Type Culture Collection, Manassas, Va.) were grown in RPMI-1640 Media (Gibco-BRL, Rockville, Md.) supplemented with 10% Fetal Bovine Serum, penicillin (614 ng/mL), streptomycin (10 μg/mL) and HEPES buffer, pH 7.2 at 37° C., 5% $CO_2$. DMSO was used as the vector for all drugs and added in the control experiments. Cell cultures were then treated with 10 μM, 1 μM, 0.1 μM or 10 μM of the drug in duplicate and allowed to incubate at 37° C., 5% $CO_2$. Cells were stained with 4% trypan blue solution in PBS, and counted under the microscope (Thomas Scientific, Fisher Scientific) in duplicate. This was repeated for 0 h, 2 h, 6 h, 12 h, 24 h, and 48 h. The data points obtained were then plotted and a point-to-point curve was drawn to determine the effect of the drug on the cells. FIG. 6A compares the cytotoxicity of hymenialdisine to compounds 2 and 3 and FIG. 6B shows the growth patterns in CEM cells at different concentrations of compound 2. The figures show that compound 3 was less cytotoxic than compound 2 or hymenialdisine.

Hymenialdisine and compounds 2 indicated similar inhibition of cell growth with $GI_{50}$ of 1.61 μM and 1.73 μM respectively, whereas compound 3 indicated weaker inhibition of cell growth ($GI_{50}$=14.3 μM). The inhibition of cell growth with compounds 1-3 could therefore account for some of the inhibition of IL-2 production seen in the Jurkat cells. IL-2 production was measured 24 hours after PMA stimulation. However, inhibition of TNF-α production was measured within 3 hours after LPS stimulation and no significant inhibition of cell growth was apparent at this time interval.

TABLE 4

Inhibition of cell growth by hymenialdisine 1 and compounds 2 and 3 in CEM leukemia cells.

| Compounds | Inhibition of cell growth $GI_{50}$, (μM)[a] |
|---|---|
| PDTC (control) | N/T |
| Hymenialdisine 1 | 1.61 (±0.062) |
| Compound 2 | 1.73 (±0.088) |
| Compound 3 | 14.3 (±2.41) |

[a]Values are means of two experiments, standard deviation is given in parentheses.

EXAMPLE 6

Figure 7A:
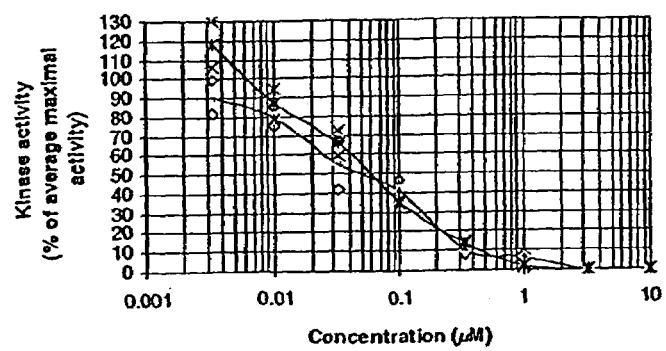
FIG. 7A is a graph showing inhibition of CDK1 and GSK-3β by hymenialdisine 1. x=CDK1 and ◊=GSK-3β.
Figure 7B:
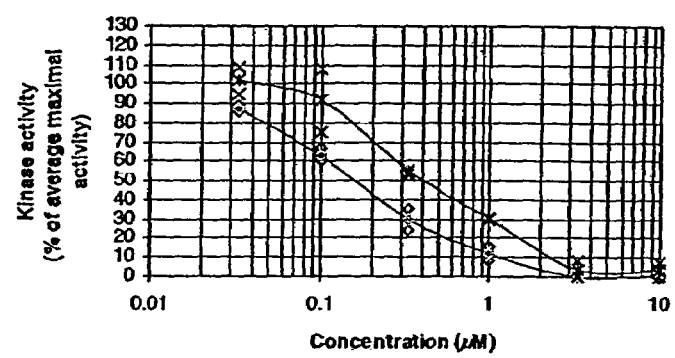
FIG. 7B is a graph showing inhibition of CDK1 and GSK-3β by compound 2. x=CDK1 and ◊=GSK-3β.
Figure 7C:
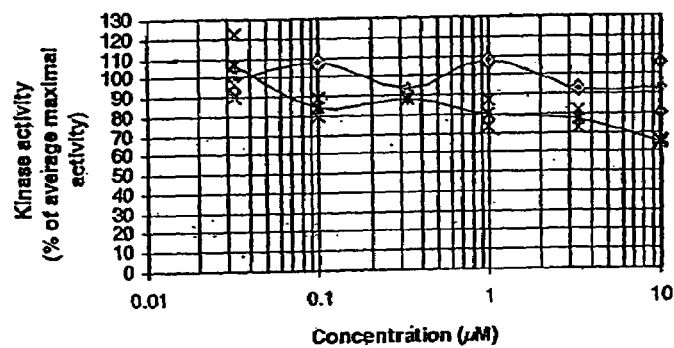
FIG. 7C is a graph showing inhibition of CDK1 and GSK-3β by compound 3. x=CDK1 and ◊=GSK-3β.

Compounds 2 and 3 were tested for inhibition of the cyclin dependent kinases CDK1 and GSK-3β using the method of Meijer et al., Chem. Biol. 7: 51-63 (2000) for showing inhibition of the kinases by hymenialdisine. The results are shown in FIGS. 7A-C and summarized in Table 5.

TABLE 5

Inhibition of CDK1 and GSK-3 by hymenialdisine 1 and compounds 2 and 3.

| Compounds | Inhibition of CDK1 $IC_{50}$, (μM) | Inhibition of GSK-3β $IC_{50}$, (μM) |
|---|---|---|
| Hymenialdisine 1 | 0.06 | 0.045 |
| Compound 2 | 0.4 | 0.15 |
| Compound 3 | >10 | >10 |

Like hymenialdisine, compound 2 inhibited CDK1 ($IC_{50}$=0.4 μM) and GSK-3β ($IC_{50}$=150 nM). Inhibition by compound 3 was less pronounced. The results are consistent with the reported X-ray crystal structure of hymenialdisine where the pyrrolic hydrogen was found to be involved in a hydrogen bonding interaction in the ATP-binding pocket (Meijer et al., Chem. Biol. 7: 51-63 (2000)).

Table 6 illustrates the comparison between the in vitro activity of indoloazepine 2, hymenialdisine and debromohymenialdisine. Compound 2 exhibits very potent inhibition of CHK2 activity in the low nanomolar range. Interestingly, unlike the natural product hymenialdisine and debromohymenialdisine, compound 2 exhibits also very potent selectivity for the checkpoint kinase CHK2.

TABLE 6

Table 6. IC$_{50}$ values for kinase inhibition by compound 2, hymenialdisine and debromohymenialdisine.

| Kinase | IC$_{50}$ (µM) compound 2 | hymenialdisine 10, 12 | debromohymenialdisine |
|---|---|---|---|
| CK1δ(h) | 1,352 | 35 | NA |
| CK2(h) | >10,000 | 7,000 | NA |
| MEK1(h) | 89 | 6[13] | 824[13] |
| PKCα(h) | 2,539 | 700 | NA |
| PKCβII(h) | 3,381 | 1,200 | NA |
| CHK1 | 237 | NA | 3,000[7] |
| CHK2 | 8 | NA | 3,500[7] |

NA: value not available

EXAMPLE 7

Figure 8:
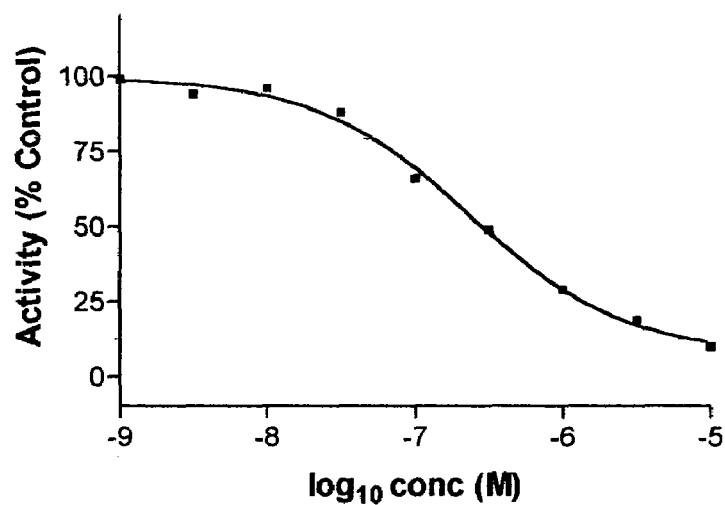
FIG. 8 is a table showing inhibition of the kinases: CK1 (h), CK2 (h), MEK1 (h), PKCa (h), PKCbII (h), CHK1 and CHK2.
Figure 9:
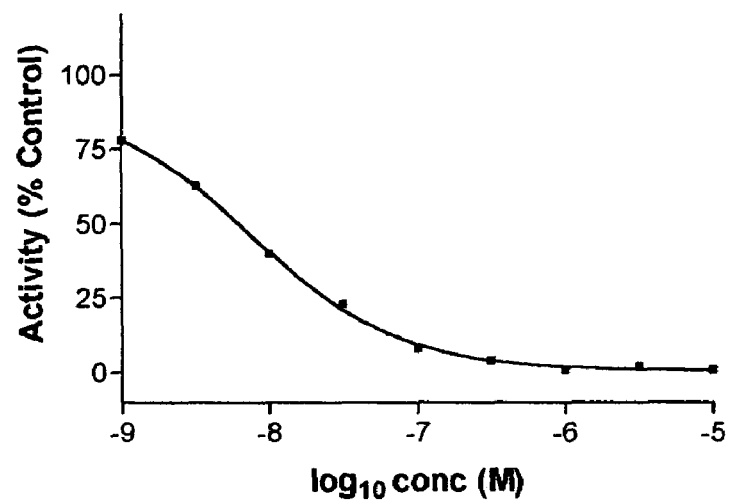
FIG. 9 is a graph showing inhibition of CHK1 and CHK2 by compound 2.

The potent inhibitory activity of the indoloazepines against checkpoint kinases Chk1 and Chk2 was determined. In vitro kinase Assay: Compound 2 was tested in vitro against the kinases indicated by Upstate, UK using a Kinase Profiler Assay according to the manufacturer's protocol. Briefly, in a final volume of 25 µl, the kinase was incubated with the desired buffer and the required polypeptide substrate, in presence of 10 mM magnesium acetate and γ-$^{33}$P-ATP (10 µM). After incubation for 40 minutes at room temperature, the reaction was stopped by the addition of 3% H$_3$PO$_4$ (5 µl). A 10 µl of the reaction was then spotted on a P30 filtermat and washed 3× in 75 mM H$_3$PO$_4$ and finally in methanol. Samples were then dried and signals counted on a scintillation counter. The indoloazepine exhibits very potent inhibition of Chk2 activity in the low nanomolar range (IC$_{50}$=8 nanoMolar). Unlike the natural product hymenialdisine and debromohymenialdisine, the indoloazepine exhibits also very potent selectivity for the checkpoint kinase Chk2. These kinase inhibition studies suggest that analogs of hymenialdisine may improve its overall kinase profile and significantly affect its kinase selectivity. The results are shown in FIGS. 8 and 9 for Chk1 and CHK2.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

I claim:

1. A method for treating an animal with an inflammatory disorder wherein said inflammatory disorder is selected from the group consisting of rheumatoid arthritis, inflammatory bowel disease, asthma, dermatosis, and organ rejection, said method comprising inhibiting production of a cytokine in cells of an animal, said cytokine selected from the group consisting of interleukin-2, TNF-α and combinations thereof, by administering to said animal a compound of the formula

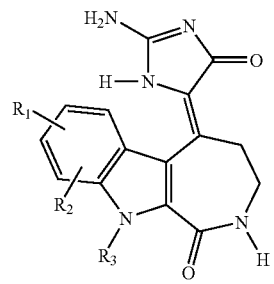

and acid amine salts thereof wherein R$_1$, R$_2$, and R$_3$ are each selected from the group consisting of hydrogen, alkyl containing 1 to 6 carbon atoms, halo, aryl, hydroxyl, amino, SH, carboxyalkyl, alkoxy and carboxyamido moieties in an amount sufficient to inhibit production of the cytokines.

2. The method of claim 1 wherein the compound inhibits a cyclin kinase selected from the group consisting of GSK-3β and CDK-1.

3. The method of claim 1 wherein R$_1$, R$_2$, and R$_3$ are each hydrogen.

4. The method of claim 1 wherein the cytokines are produced by activation of a κF-κB pathway.

5. The method of claim 1 wherein the animal is a human.

6. The method of claim 1 wherein said administering is by parenteral administration.

* * * * *

```
                    SEQUENCE LISTING

<160> NUMBER OF SEQ ID NOS: 1

<210> SEQ ID NO 1
<211> LENGTH: 22
<212> TYPE: DNA
<213> ORGANISM: Artificial
<220> FEATURE:
<223> OTHER INFORMATION: NF-kB consensus oligonucleotide

<400> SEQUENCE: 1
agttgagggg actttcccag gc                                         22
```